(12) United States Patent
Hayashizaki

(10) Patent No.: US 7,374,882 B2
(45) Date of Patent: May 20, 2008

(54) METHOD FOR BASE SEQUENCING AND BIOLOGICALLY ACTIVE NUCLEIC ACIDS

(75) Inventor: Yoshihide Hayashizaki, Tsukuba (JP)

(73) Assignee: Riken, Saitama (JP)

( * ) Notice: Subject to any disclaimer, the term of this patent is extended or adjusted under 35 U.S.C. 154(b) by 495 days.

(21) Appl. No.: 10/432,991

(22) PCT Filed: Nov. 11, 2001

(86) PCT No.: PCT/JP01/10400

§ 371 (c)(1),
(2), (4) Date: Aug. 14, 2003

(87) PCT Pub. No.: WO02/44195

PCT Pub. Date: Jun. 6, 2002

(65) Prior Publication Data

US 2004/0115665 A1    Jun. 17, 2004

(51) Int. Cl.
*C12Q 1/68*    (2006.01)
*C07H 21/00*    (2006.01)
*C07H 21/02*    (2006.01)

(52) U.S. Cl. .................... 435/6; 536/23.1; 536/24.3; 536/24.33; 435/91.1; 435/91.2

(58) Field of Classification Search .............. 435/6, 435/91.1, 91.2; 536/23.1, 24.3, 24.33
See application file for complete search history.

(56) References Cited

U.S. PATENT DOCUMENTS

| 5,432,272 A | | 7/1995 | Benner |
| 5,681,702 A | * | 10/1997 | Collins et al. ................. 435/6 |
| 5,849,542 A | * | 12/1998 | Reeve et al. ............... 435/91.1 |
| 6,001,983 A | | 12/1999 | Benner |
| 6,037,120 A | * | 3/2000 | Benner ......................... 435/6 |

OTHER PUBLICATIONS

Roberts, C., et al. Tetrahedron Letters, Elsevier Science Publishers, Amsterdam, NL, vol. 36, No. 21, May 22, 1995, pp. 3601-3604.
Hermann, T., et al. SCIENCE, vol. 287, Feb. 4, 2000, pp. 820-825.
Collins, M. L., et al. Nucleic Acids Research, vol. 25, No. 15, 1997, pp. 2979-2984.
Tuerk, C., et al. Science, American Association for the Advancement of Science, US, vol. 249, Aug. 3, 1990, pp. 505-510.

* cited by examiner

*Primary Examiner*—Jezia Riley
(74) *Attorney, Agent, or Firm*—Birch, Stewart, Kolasch & Birch, L.L.P.

(57) ABSTRACT

Aptamers are nucleic acids and similar molecules, such as peptide-nucleic acids, that specifically bind to a ligand such as a protein or peptide. The present invention provides aptamers comprising at least one base capable of base pairing and different from the standard Watson-Crick bases. The present invention also relates to a method for preparation of such aptamers and to methods for sequencing nucleic acids that comprise at least one base capable of base pairing and different from the standard Watson-Crick bases.

30 Claims, 5 Drawing Sheets

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: a reverse
                        3' primer

<400> SEQUENCE: 1
agcggataac aatttcacac                                                  20

<210> SEQ ID NO 2
<211> LENGTH: 70
<212> TYPE: DNA
<213> ORGANISM: Artificial Sequence
<220> FEATURE:
<223> OTHER INFORMATION: Description of Artificial Sequence: an
                        oligonucleotide template

<400> SEQUENCE: 2
cacgacgttg taaaacgacg gccagtgtta cggcattgcc gatgacgatg gtgtgaaatt      60
gttatccgct                                                             70

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: a sequence
                        sequenced in Example 2

<400> SEQUENCE: 3
ttcacaccat cgtcatcggc aatgccg                                          27

<210> SEQ ID NO 4
<211> LENGTH: 1214
<212> TYPE: DNA
<213> ORGANISM: Mus musculus
<220> FEATURE:
<221> NAME/KEY: CDS
<222> LOCATION: (300)..(935)

<400> SEQUENCE: 4
gatgttcaag gtgagaatgt ggagccgggt cacagctgtc attgtcccct ctcagcctcc      60
aggagccctc cccacgctcc cgggcgtctt tttgcgggac cagactcggt tcctcctgag     120 gccttttca cctccgggct aaattctggc ttggcggcgg ttcattcagc actcggtacc     180
agcacctgtg aggttgtgga gtgaaaccct agattggtgg gatcggccct ttgagctctc     240
tcgcgaatga aacactttga aaagttaaaa cgcctctatc gtgcccacct cctcggcta     299 atg ccc ttt tgg ggt tgt ggg gag gat gaa gcc agg tct ggg cgc tgc      347
Met Pro Phe Trp Gly Cys Gly Glu Asp Glu Ala Arg Ser Gly Arg Cys
```

```
agg gta att cag aga tct gtg ggg cca gcc agc ctg agc ctg ctc acc    395
Arg Val Ile Gln Arg Ser Val Gly Pro Ala Ser Leu Ser Leu Leu Thr
             20                  25                  30 ttc aga gtc tat gca gca ccc aaa aag gac tcg cct cac aaa agt tac    443
Phe Arg Val Tyr Ala Ala Pro Lys Lys Asp Ser Pro His Lys Ser Tyr
         35                  40                  45 atg aag atc gat gag ctt tca ctc tac tca gtt cct gag ggt caa tct    491
Met Lys Ile Asp Glu Leu Ser Leu Tyr Ser Val Pro Glu Gly Gln Ser
 50                  55                  60 aaa tat gtg gag gag cca agg act caa ctt gaa gaa aac atc tca caa    539
Lys Tyr Val Glu Glu Pro Arg Thr Gln Leu Glu Glu Asn Ile Ser Gln
 65                  70                  75                  80 ctc cga cat cat tgt gag cca tat aca agt ttc tgt cag gaa ata tac    587
Leu Arg His His Cys Glu Pro Tyr Thr Ser Phe Cys Gln Glu Ile Tyr
                 85                  90                  95 tcc cat act aaa ccc aag gtg gat cac ttt gtc cag tgg gga gta gac    635
Ser His Thr Lys Pro Lys Val Asp His Phe Val Gln Trp Gly Val Asp
            100                 105                 110 aac tat aac tat ctt caa aat gcg cct cct gga ttt ttc cca aga ctc    683
Asn Tyr Asn Tyr Leu Gln Asn Ala Pro Pro Gly Phe Phe Pro Arg Leu
        115                 120                 125 ggt gtt att ggt ttt gct ggt ttt gtt gga ctc ctt ttt gct aga ggt    731
Gly Val Ile Gly Phe Ala Gly Phe Val Gly Leu Leu Phe Ala Arg Gly
    130                 135                 140 tca aaa ata aag aag ctg gtg tat cct cct ttt ttc atg gga tta ggt    779
Ser Lys Ile Lys Lys Leu Val Tyr Pro Pro Phe Phe Met Gly Leu Gly
145                 150                 155                 160 gcc tct gtc tat tac cca caa caa gcc atc acc att gcc cag atc act    827
Ala Ser Val Tyr Tyr Pro Gln Gln Ala Ile Thr Ile Ala Gln Ile Thr
                165                 170                 175 ggg gag aag tta tat gac tgg gga tta cga ggg tac ata gtt ata gaa    875
Gly Glu Lys Leu Tyr Asp Trp Gly Leu Arg Gly Tyr Ile Val Ile Glu
            180                 185                 190 gat ttg tgg aag caa aat ttt cag aag cca gga aat gtg aag aat tca    923
Asp Leu Trp Lys Gln Asn Phe Gln Lys Pro Gly Asn Val Lys Asn Ser
        195                 200                 205 cct gga aat aaa tagaaaactc catgctctgc ccatttcaat cagttatagg        975
Pro Gly Asn Lys
    210 taaacattgg aaacttcaga cagtaaatca gtatttctac agacaaatgg cgaaatcagt   1035 attggatata gtaaactggc tttcttcagg aaaaacaaca ctaagccttt tgctcttttt   1095 gggtgatgcc atattacagg ccaactaatc tgcaatcttt cacatggaaa taatgtacaa   1155 gccttagaac tcctcattct tataccacta tttatgtaca taattaaact ccagattcc    1214

<210> SEQ ID NO 5
<211> LENGTH: 212
<212> TYPE: PRT
<213> ORGANISM: Mus musculus

<400> SEQUENCE: 5

Met Pro Phe Trp Gly Cys Gly Glu Asp Glu Ala Arg Ser Gly Arg Cys
 1               5                  10                  15

Arg Val Ile Gln Arg Ser Val Gly Pro Ala Ser Leu Ser Leu Leu Thr
             20                  25                  30

Phe Arg Val Tyr Ala Ala Pro Lys Lys Asp Ser Pro His Lys Ser Tyr
         35                  40                  45
```

```
Met Lys Ile Asp Glu Leu Ser Leu Tyr Ser Val Pro Glu Gly Gln Ser
     50                  55                  60
Lys Tyr Val Glu Glu Pro Arg Thr Gln Leu Glu Glu Asn Ile Ser Gln
 65                  70                  75                  80
Leu Arg His His Cys Glu Pro Tyr Thr Ser Phe Cys Gln Glu Ile Tyr
                 85                  90                  95
Ser His Thr Lys Pro Lys Val Asp His Phe Val Gln Trp Gly Val Asp
                100                 105                 110
Asn Tyr Asn Tyr Leu Gln Asn Ala Pro Pro Gly Phe Pro Arg Leu
            115                 120                 125
Gly Val Ile Gly Phe Ala Gly Phe Val Gly Leu Leu Phe Ala Arg Gly
    130                 135                 140
Ser Lys Ile Lys Lys Leu Val Tyr Pro Pro Phe Phe Met Gly Leu Gly
145                 150                 155                 160
Ala Ser Val Tyr Tyr Pro Gln Gln Ala Ile Thr Ile Ala Gln Ile Thr
                165                 170                 175
Gly Glu Lys Leu Tyr Asp Trp Gly Leu Arg Gly Tyr Ile Val Ile Glu
            180                 185                 190
Asp Leu Trp Lys Gln Asn Phe Gln Lys Pro Gly Asn Val Lys Asn Ser
    195                 200                 205
Pro Gly Asn Lys
    210

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: a primer

<400> SEQUENCE: 6
gtgcccacct cctcggcata tgccc                                          25

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: a primer

<400> SEQUENCE: 7
tgaagtttcc aatgggatcc tataac                                         26

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: a left
      flanking region

<400> SEQUENCE: 8
tgtaaaacga cggccagt                                                  18

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: a right
      flanking region
```

<400> SEQUENCE: 9
gtgtgaaatt gttatccgct                                           20

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: a primer

<400> SEQUENCE: 10
tgtaaaacga cggccagt                                             18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: complement
         of the 3' primer

<400> SEQUENCE: 11
gtgtgaaatt gttatccgct                                           20

<210> SEQ ID NO 12
<211> LENGTH: 81
<212> TYPE: DNA
<213> ORGANISM: Artificial Sequence
<220> FEATURE:
<223> OTHER INFORMATION: Description of Artificial Sequence: a sequence
         of Template 1

<400> SEQUENCE: 12
tgtaaaacga cggccagtgc gtaacggggt ctatgttccc gcacaccgtg gcaaaactgt    60
gtgaaattgt tatccgctgc t                                             81

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: a sequence
         of the aptamer portion

<400> SEQUENCE: 13
gcgtaacggg gtctatgttc ccgcacaccg tggcaaaact                         40

<210> SEQ ID NO 14
<211> LENGTH: 94
<212> TYPE: DNA
<213> ORGANISM: Artificial Sequence
<220> FEATURE:
<223> OTHER INFORMATION: Description of Artificial Sequence: a primer

<400> SEQUENCE: 14
tgccatttca ttacctcttt ctccgcaccc gacatagatg acactactac ggtatgatcc    60
tatggagaac gctcagcgga taacaatttc acac                               94

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: a spacer

<400> SEQUENCE: 15
gcacccgaca tagatgacac tactacggta tgatcctatg gagaacgctc                50

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: the
      annealing site to single strand DNA

<400> SEQUENCE: 16
aggggataac aatttcacac                                                 20

<210> SEQ ID NO 17
<211> LENGTH: 78
<212> TYPE: DNA
<213> ORGANISM: Artificial Sequence
<220> FEATURE:
<223> OTHER INFORMATION: Description of Artificial Sequence: a negative
      control aptamer

<400> SEQUENCE: 17
tgtaaaacga cggccagttt ccggagtcac ggctgcgggc cgtctgagcc gtttgcacgt      60
gtgaaattgt tatccgct                                                   78

<210> SEQ ID NO 18
<211> LENGTH: 17
<212> TYPE: DNA
<213> ORGANISM: Artificial Sequence
<220> FEATURE:
<223> OTHER INFORMATION: M13 forward primer

<400> SEQUENCE: 18
gtaaaacgac ggccagt                                                    17

<210> SEQ ID NO 19
<211> LENGTH: 60
<212> TYPE: DNA
<213> ORGANISM: Artificial Sequence
<220> FEATURE:
<223> OTHER INFORMATION: Synthetic oligonucleotide template

<400> SEQUENCE: 19
ctatgaccat ggtctcgcct tggtctttag gtgacactat tttactggcc gtcgttttac     60

<210> SEQ ID NO 20
<211> LENGTH: 40
<212> TYPE: DNA
<213> ORGANISM: Unknown
<220> FEATURE:
<223> OTHER INFORMATION: Description of Unknown: nucleotide sequence as
      shown in the electropherogram of Figure 5

<400> SEQUENCE: 20
atagtgtcac ctaaagacca aggcgagacc atggtcatag                           40

METHOD FOR BASE SEQUENCING AND BIOLOGICALLY ACTIVE NUCLEIC ACIDS

FIELD OF THE INVENTION

The present invention relates to a nucleic acid comprising at least one base capable of base pairing and different from the standard Watson-Crick bases. The present invention also relates to a method for preparation of such a nucleic acid.

The invention also relates to a method for the sequencing of nucleic acids comprising at least one base capable of base pairing and different from the standard Watson-Crick bases.

BACKGROUND ART

Aptamers are nucleic acids that specifically associate with a ligand. Aptamers can be selected in vitro by a technique known as SELEX (Systematic Evolution of Ligands by Exponential Enrichment). SELEX is a method for optimizing nucleic acids for high-affinity to given ligands starting from random sequence libraries (Hermann T. and Patel D. J., February 2000, *Science,* Vol.287:820-825; Tuerk C. and Gold L., 1990, *Science,* Vol.249: 505).

Predominantly unstructured in solution, aptamers fold upon associating with their ligands into molecular architectures in which the ligand becomes specifically complexed with the nucleic acid. Because the evolutionary pressure on aptamer sequences during selection is directed primarily toward the binding of the ligands, the three-dimensional structures of aptamer complexes reflect highly optimized scaffolds for specific ligand recognition.

The architectures of aptamer complexes are valuable for the study of molecular recognition processes and yield a diversity of three-dimensional motifs, which recur in biologically relevant nucleic acid folds. It has been reported that small molecule RNA complexes are especially helpful for the rational exploration of RNA as a drug target. Drug design approaches for cellular RNA targets that combine structural data in RNA complexes with modelling techniques are especially promising, given the extraordinary success of molecular modelling of higher-order RNA architectures (Hermann and Patel, 2000). Nucleic acid aptamers provide unique tools in medicinal diagnosis and biotechnology and serve as therapeutics (Hermann and Patel, 2000). For example, aptamers that bind and inhibit human thrombin have been reported in Bock L. C. et al, 1992, *Nature,* Vol.355: 564-566.

However, there is a limitation in the use of aptamers because the structurally uniform four nucleotides are limited in possible alternative ways to pack around arbitrary ligands (Hermann and Patel, 2000).

There is therefore the need in this field of science of new solutions for the availability of aptamers which allow the selection of a highly diverse and differentiated kind of ligands.

The invention disclosed in the present application solves this problem in the art.

SUMMARY OF THE INVENTION

The present inventor has surprisingly found that nucleic acid aptamers comprising at least one base capable of base pairing and different from the standard Watson-Crick (W-C) bases are particularly useful for the selection of new and specific ligands.

Accordingly, the present invention relates to a method for the preparation of nucleic acid aptamers comprising at least one base capable of base pairing and different from the standard Watson-Crick bases, wherein the standard Watson-Crick bases are adenine (A), cytosine (C), guanine (G), thymidine (T) and uracil (U).

The method comprises:
a) providing a specific, interesting ligand;
b) synthesizing a pool of nucleic acid aptamers comprising at least one base capable of base paring and different from the standard Watson-Crick bases;
c) mixing this pool of aptamers with the specific ligand;
d) selecting and amplifying a specific aptamer that binds to the specific ligand.

Accordingly, the present invention also relates to a specific aptamer prepared as above.

The present invention also relates to a method for recovering and determining a specific ligand comprising:
i) providing at least one specific aptamer comprising at least one base capable of base pairing and different from the standard Watson-Crick bases;
ii) mixing this aptamer with a pool of ligands (for example human serum or proteins therefrom);
iii) recovering and determining the specific ligand bound to the specific aptamer.

According to another aspect of the present invention, the at least one aptamer according to the invention, can be fixed, directly or by means of a spacer sequence, to an insoluble substrate, for example a chip. The aptamer fixed on the substrate is then treated with a ligand mixture (for instance human serum) and the ligand bound to the aptamer is then recovered. According to a particular solution, the substrate comprises several specific aptamers according to the invention fixed on it. These specific aptamers fixed on a substrate are treated with a mixture of ligands and the ligands specifically bound to these aptmers are then recovered from the substrate. Preferably, the mixture of ligands is labeled and the quantitative amount of the ligand bound to aptamer can be determined.

Accordingly, the invention relates to a detection method for the detection of specific ligand, comprising:
I) selecting at least one specific aptamer capable of binding to a searched specific ligand, the at least one specific aptamer being available in solution or fixed on an insoluble substrate;
II) mixing the at least one specific aptamer with a biological sample;
III) detecting the presence and/or quantity of the searched specific ligand specifically bound to the at least one specific aptamer.

As a particular embodiment of the above method, the detection method can be a diagnostic method.

Accordingly, the present invention also relates to a detection or diagnostic kit comprising (i) at least one specific aptamer or (ii) one or more substrates having one or more specific aptamers fixed on it (them), and optionally one or more labels for labelling a ligand mixture.

Further, the invention relates to a pharmaceutical composition comprising the aptamer according to the invention in presence of a pharmaceutically suitable diluent, excipient and/or carrier.

According to another aspect, the invention relates to a method for sequencing nucleic acids comprising at least one base capable of base pairing and different from the standard Watson-Crick bases.

BRIEF DESCRIPTION OF THE DRAWINGS

FIG. 1 shows that when isoG and isoC are used and the concentration of isoG and isoC is lower than the standard W-C bases A, C, G, T (run B) the sequencing can be performed accurately.

DETAILED DESCRIPTION OF THE INVENTION

Figure 1:
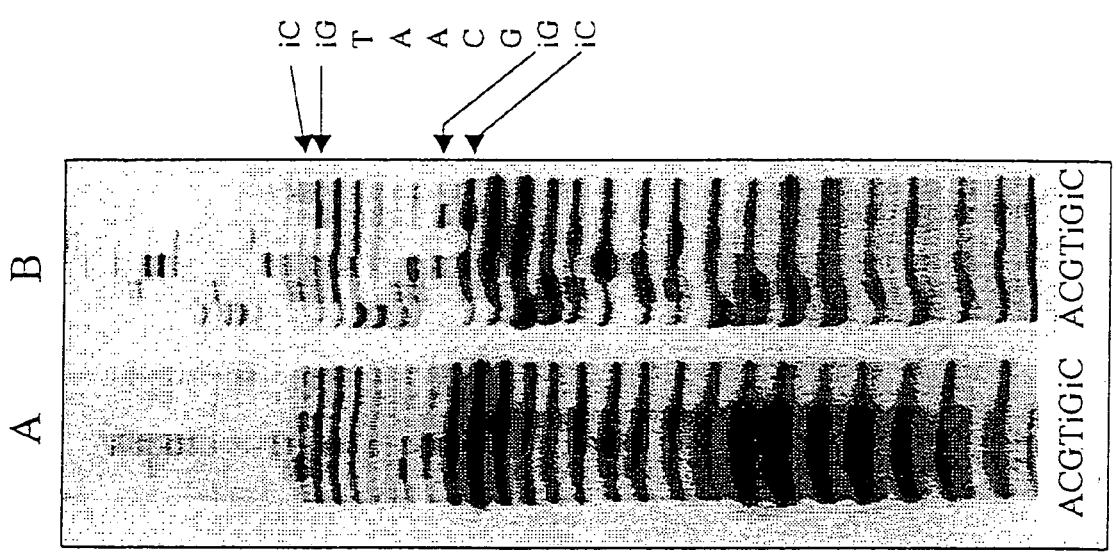
FIG. 1 shows an autoradiogram of DNA sequencing by the dideoxy method (Sanger) of Example 2. Column A) shows a sequencing reaction carried out under the standard conditions, wherein the concentrations of the non-standard W-C bases used as substrate (isoG and isoC), were the same as the standard bases (83.3 µM). In B) the sequencing reaction was the same as A) except that the concentrations of isoG and isoC substrates were reduced to 40 µM. iC and iG in FIG. 1 represent isoC and isoG, respectively. The capital letter at the bottom represents its corresponding dideoxynucleotide comprised in the sequencing reaction.

According to a first aspect, the present invention provides a method for the preparation of new nucleic acid aptamers comprising at least one base capable of base pairing and different from the standard Watson-Crick bases. These new aptamers are particularly useful for the selection of new and specific ligands.

The preparation of aptamers according to the invention can be performed according to the SELEX protocol known in the art as described for example in detail in Tuerk & Gold, 1990, *Science* 249:505; Tuerk et al., 1992, *Proc. Acad Sci. USA* 89:6988.

The ligand for aptamer selection can be any product useful as a ligand and able to be recognized by the aptamer according to the invention. Examples of ligands are reported in Hermann and Patel, 2000. The ligand can for example be an amino acid, a peptide, a protein, a lipid, an oligosaccharide, an alkaloid, a terpene, a co-enzyme, an antibiotic, or a derivative or complex of such molecules.

The ligand can be synthesized according to known techniques, In the case of a peptide or protein it can be produced on a peptide synthesizer or by recombinant DNA technology, or can be purified from a biological tissue.

The ligand can be a protein or a modified protein. For example the protein might be phosphorylated or non-phosphorylated, and/or glycosylated or non-glycosylated. The protein ligand can be produced according to the recombinant techniques known in the art, and can be made from a full-length cDNA library (for example using the methodology described in U.S. Pat. No. 6,143,528; in Carninci et al., 1996, *Genomics*, 37:327-336; Carninci et al., 1997, *DNA Research*, 4, 61-66; Carninci et al., October 2000, *Genome Research*, 1617-1630).

The ligand according to the invention is not limited by molecular weight, but preferably it has a molecular weight less than 5,000 daltons.

The pool of aptamers according to the invention comprising aptamers having at least one base capable of base pairing and different from the standard W-C bases can be prepared according to standard techniques known in the art, for example by an automated synthesizer, for example EXPEDITE 8909 using a standard protocol. Preferably, the pool synthesized is a random pool of single-stranded nucleic acids comprising a region of random sequence (which represents the random aptamer pool) flanked by defined regions, which will be recognized by specific primers for amplification of the template. The template generated can be preferably amplified, for example, using several PCR cycles. The PCR can be performed under standard conditions, however the concentration of the triphosphate nucleosides can be modified according to the particular modified base different from a standard W-C bases. For instance, as reported in Example 3, when the bases different from the standard W-C bases used were isoC and isoG, the standard concentration of standard W-C base (A, C, G, T) was 200 µM, while the isoC and isoG concentrations were 100 µM.

Other amplification methodologies than PCR that are available in the state of the art can be used for the preparation of the template according to the invention. For example, LAMP (Loop-mediated Isothermical Amplification)(Notomi et al., 2000, *Nucleic Acids Research*, 28:page e63); TMA (Transcriptional Mediated Amplification)(Kamisango, K. et al., 1999, *J.Clin.Microbiol.*, 37:310-314); ICAN (Isothermal and Chimeric primer-initiated Amplification of Nucleic Acid)(TAKARA SHUZO CO, LTD, Bio-Japan 2000, September 26-28); SDA methodology (Walker et al., 1992, *Nucleic Acids Res.*, Vol.20:1691-1696).

The composition of the aptamer comprised in the template pool according to the invention will be as described below.

In step c) the aptamer pool according to the invention is mixed with the specific ligand prepared in step a).

The specific aptamer bound to the specific ligand is recovered and amplified (step d).

The nucleic acid aptamer, according to the invention, making up the pool of aptamers or pool of template comprising a region of random sequences of step b) is described as follows.

The aptamer is a nucleic acid comprising at least one base different from the standard W-C bases, wherein the standard W-C bases are defined as A, C, G, T or U. Preferably, the aptamer comprises at least one base different from the standard W-C bases and at least one standard W-C base.

This base different from the standard W-C bases can be any base capable of base pairing. It can be a non-standard W-C base as defined in Benner, S. A. U.S. Pat. No. 5,432,272, for example isoG and/or isoC (Roberts et al., 1995, *Tetrahedron Letters*, Vol.36, No.21, pp.3601-3604, Elsevier Science Ltd), or can be a non-W-C base and capable of hydrophobic base pairing.

Figure 3:
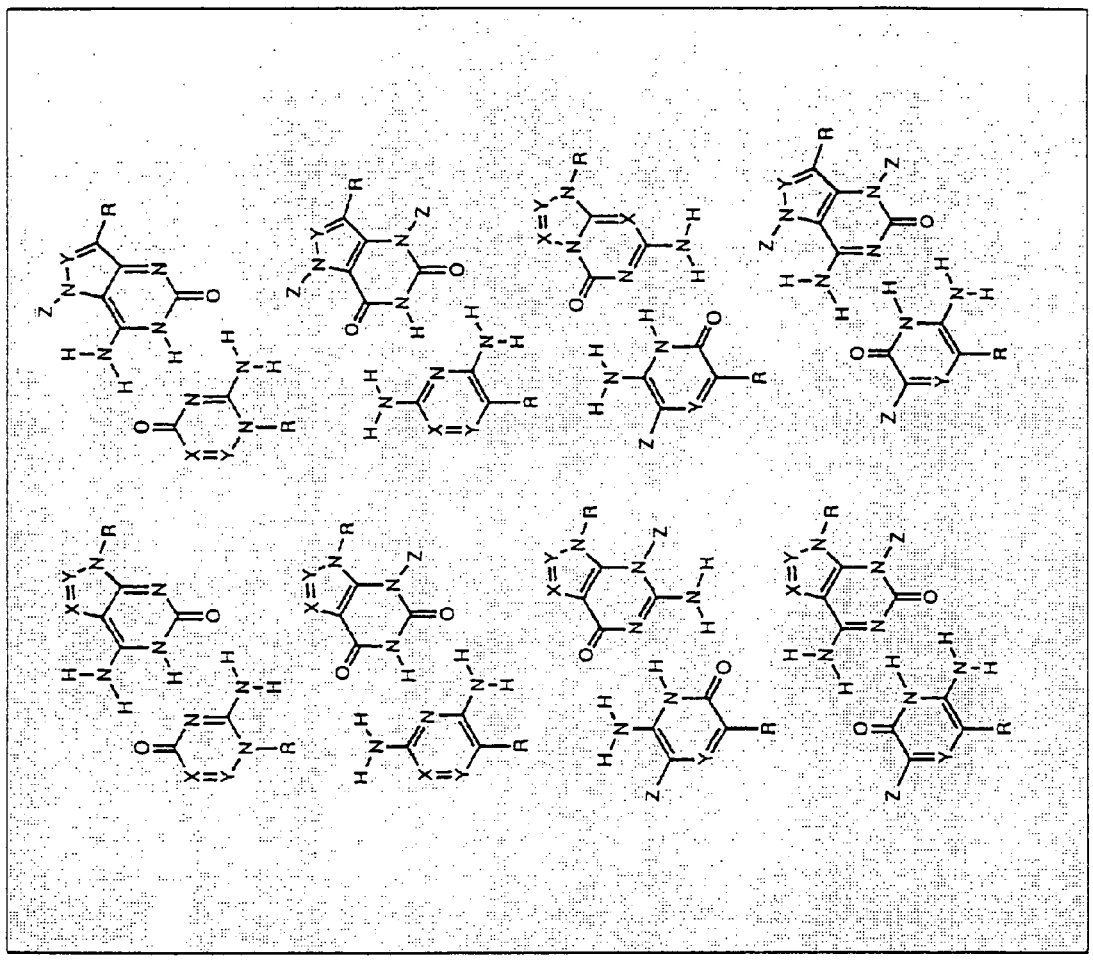
FIG. 3 shows exemplary structural formulae of heterocyclic bases different from standard Watson-Crick bases ("non-standard bases"). R designates the point of attachment of the base to position 1 of a ribose or deoxyribose ring, X is either a nitrogen atom or a carbon atom bearing a substitutent Z. Z is either a hydrogen, an unfunctionalized lower alkyl chain, or a lower alkyl chain bearing an amino, carboxyl, hydroxyl, thiol, aryl, indole, or imidazolyl group, Y is either N or CH, and each ring contains no more than three nitrogens consecutively bonded (according to Benner, S. A. U.S. Pat. No. 5,432,272).

Examples of non-standard W-C bases are iso-C; iso-G; 2,6-diaminopyrimidine;
xanthine; 6-amino-5-substituted pyrazin-2(1H)-one;
1-methyl-pyrazolo[4,3-d]pyrimidine-5,7(4H,6H)-dione; 5-aza-7-deazaguanine;
6-amino-3-substituted pyrazin-2(1H)-one;
3-amino-1-methylpurin-2-one-;2,4-diamino-5,6-dihydropyrimidine;
2-amino-6-(N,N-dimethylamino)purine; pyridin-2-one; other heterocyclic bases selected from the group consisting of the structural formulae of FIG. 3. In particular, the bases 2-amino-6-(N,N-dimethylamino)purine and pyridin-2-one are disclosed in Ishikawa, M. et al., 1999, *Nucleic Acids Symp Ser,* 42:125-126.

Examples of non-W-C bases (for instance exhibiting hydrophobic base pairing) are 3-methyl isocarbostyril; 5-methyl isocarbostyril; 7-propynyl isocarbostyril; m-xylene; 1,3,4-trimethylbenzene; 2-methylanaphthalene; 1,4-dimethylnaphthalene; 1-methylnaphthalene; naphthalene; 7-azaindole; isocarbostyril; 6-methyl-7-asaindole; 3-propynyl-7-azaindole; imidazopyridine; pyrrolopyridine. In particular, the base 7-propynyl isocarbostyril, which is capable of pairing with itself, is described by Robert F. Service in *Science,* July 2000, Vol.289:232-235.

The aptamer comprising the at least one base capable of base pairing and different from standard W-C bases according to the invention shows a high variability of possible combinations. The nucleic acid aptamer according to the invention comprises at least one base capable of base pairing and different from the standard W-C bases, preferably comprises at least one base capable of base pairing and different from the standard W-C bases and at least one standard W-C base (A, C, G, T or U). However, the number of bases capable of base pairing and different from the standard W-C bases is not limited. A nucleic acid aptamer according to the invention can therefore comprise, for example, 6 different bases, preferably A, C, G, T, isoG and isoC. However, it can also comprise 8, 10, 12, 14 or more different bases (see U.S. Pat. No. 5,432,272).

The use of bases capable of base pairing and different from the standard W-C bases according to the invention allows the preparation of specific aptamers having a higher variability than aptamers available in the state of the art. In fact, if we consider nucleic acids having different length, the number of different aptamers than it is possible to prepare using the four standard W-C bases is much lower than the number of different aptamers that can be prepared using the bases different from standard W-C bases according to the invention, as reported in the Table 1 below. In Table 1, "4 W-C St. bases" relates to a nucleic acid comprising only the W-C standard bases, "4 W-C st.+iG+iC" relates to a nucleic acid comprising the 4 standard W-C bases and 2 bases different from the standard W-C bases, for example isoG (iG) and isoC (iC).

TABLE 1

|  | 4 W-C st. bases | 4 W-C st. + iG + iC |
| --- | --- | --- |
| 4 mer | 256 | 1,296 |
| 6 mer | 4,096 | 46,656 |
| 8 mer | 65,536 | 1,679,616 |
| 10 mer | 1,048,576 | 60,466,176 |

As is clear from the Table 1, the variability of the aptamer disclosed by the present invention is a considerably improved compared to the aptamers available in the state of the art.

The aptamer according to the invention can be DNA, RNA or protein nucleic acid (PNA), and can be a single, double or triplex stranded nucleic acid. The aptamer can be of different lengths, preferably 12-300 bases.

The aptamer prepared according to the present invention can be used for recovering and determining a specific ligand from a pool of ligands (or a mixture of ligands) or from a biological sample. Such a method comprises:
  i) providing at least one specific aptamer comprising at least one base capable of base pairing and different from standard W-C bases, as above described;
  ii) mixing this aptamer with a pool of ligands or biological sample;
  iii) recovering and determining the specific ligand bound to the specific aptamer.

The at least one specific aptamer of step i) is prepared as above described according to steps a)-d). One specific aptamer can be used, or more than one different specific aptamers can be used at the same time, for instance if they are fixed on a insoluble substrate, for example a chip. Therefore, the aptamer can be used in solution or fixed or bound to an insoluble substrate, preferably fixed on a chip substrate.

The pool of ligands of step ii) can be any pool or mixture of ligands prepared with conventional methods known in the technique or can be a biological sample. The ligand comprised in the pool of ligands can be preferably selected from amino acids, peptides, proteins, lipids, oligosaccharides, alkaloids, terpenes, co-enzymes, antibiotics, and their derivatives and their complexes.

When the ligand pool comprises proteins and/or peptides, they can be modified or non-modified, phosphorylated or non-phosphorylated, and/or glycosylated or non-glycosylated. Accordingly, the specific aptamer is able to distinguish between phosphorylated and non-phosphrylated, and/or between glycosylated and non-glycosylated and/or between modified and non-modified ligand proteins and peptides.

The ligands comprising the pool of ligands can be preferably labeled by contacting the pool of ligands with a label. The label can be any label able to be detected known in the art, for instance an isotope, chromophore or fluorophore label. Alternatively, a ligand can be detected by an antibody that specifically binds to the ligand.

In step iii) the ligand bound to the aptamer is detected and optionally separated from the aptamer and recovered. The detection can be either qualitative or quantitative. It is clear that in cases that more than one specific aptamer is used (for instance using a chip comprising several specific aptamers, different from each other, fixed on it) more than one ligand, each specific and bound to the specific aptamer, might be recovered. The selection can be done, for example, by detecting the label or labels introduced as above described. The detection, separation and recovery are performed according to the techniques known in the art.

As said above, the aptamer or aptamers according to the invention can be used in solution, or can be preferably fixed on an insoluble substrate, for example on a chip substrate. An insoluble substrate according to the invention can be any kind of surface of an insoluble substance, for example, beads, syringe, capillary, tube, plate. The insoluble substrate is preferably a chip (U.S. Pat. No. 5,525,464). The insoluble substrate can be used in a chromatographic format.

The aptamer(s) can be fixed to the insoluble substrate, preferably a chip substrate, according to standard techniques, for example synthesized on a chip as described by U.S. Pat. No. 5,837,832, or prepared and then fixed on a chip as described in EP 1041160. The aptamer can be fixed directly to the chip substrate or by means of a spacer or a linker sequence, for example as described in Example 4.

The aptamer fixed on the substrate is then treated with a ligand mixture (for instance human serum) and the ligand bound to the aptamer is then recovered and characterized. According to a particular solution, the chip has fixed on it several specific aptamers according to the invention. Preferably, the mixture of ligands is labeled and the quantitative amount of the ligand bound to aptamer can be determined.

Accordingly, the invention relates to a detection method for the detection of specific ligand, comprising:

I) selecting at least one specific aptamer, according to the invention, capable of binding to at least one desired specific ligand, the at least one specific aptamer being available in solution or fixed on a substrate II) mixing the at least specific aptamer with a biological sample;

III) detecting the presence and/or quantity of the at least one specific ligand.

As a particular embodiment of the above method, the detection method can be a diagnostic method for the detection of a ligand selected from a biological sample. An example of diagnostic methods according to the invention is a method for the detection of a disease, wherein the presence or amount of the specific ligand is related to a particular disease. The method can be used, for example, for detecting the concentration of cholesterol, testing for the drug concentration in the blood and other diagnostic utilities known in the state of the art. The ligand can also be, for example, a membrane receptor with a particular function or activity, the modification of which has influence on the expression of a particular disease.

The biological sample can be of any biological source e.g., vegetal or animal. For example, it can be a serum or a blood sample from a patient.

Accordingly, the present invention also relates to a detection or diagnostic kit comprising at least one specific aptamer according to the invention, or at least one substrate having one or more specific aptamers fixed on it, and optionally one or more labels for labeling the ligand pool or biological sample, as above described.

The specific aptamer according to the invention is particularly useful as disclosed for example in Hermann and Patel, 2000. For instance it can be used as a drug and for therapeutic treatment.

According to another aspect, the invention is a pharmaceutical composition comprising the aptamer according to the invention in presence of a pharmaceutically suitable diluent, excipient and/or carrier. The invention also relates to a therapeutic method for the treatment of disease comprising the administration of the aptamer according to the invention, preferably in form of pharmaceutical composition as described above.

The use of aptamers for treatments in vivo is disclosed in literature (for example, Hicke et al., *The Journal of Clinical Investigation*, October, 2000, Vol.106, No.8; Watson et al., *Antisense Nucleic Acid Drug Dev.*, April,2000: 10(2):63-75; and Floege et al., *American Journal of Pathology*, Vol.154, No.1, January,1999).

In Floege et al, in vivo effects of a nuclease-resistant high-affinity oligonucleotide aptamer were evaluated in a rat mesangioproliferative glomerulonephritis model. Twice-daily intravenous (i.v.) injections from 3 to 8 days after disease induction of a 2.2 mg/kg PDGF-B aptamer, coupled with 40-kd polyethylene glycol (PEG), led to a reduction of glomerular mitoses, a reduction of proliferating mesangial cells, etc.

In other experiments, Floege-et al also observed that doses of PDGF-B aptamer as low as 2 mg total were sufficient for the treatment.

Accordingly, the aptamer according to the present invention can be used for the preparation of a formulation as above described, to be administered in different routes, preferably by injection, comprising an amount of aptamer or aptamer substance according to the body weight and physiological conditions of the patient, however 2 mg/kg of body weight or more can be administered.

The aptamer according to the invention can be sequenced.

The inventor has found that the classical sequencing method known in the art, for example based on the Sanger method, (Sanger et al., 1977, *Proc.Natl.Acad.Sci. USA*, 74:5463-5467; Sanger et al., 1980, *J.Mol.Biol.*, 143:161-178; Tabor and Richardson, 1989a, *J.Biol.Chem.*, 264:6447-6458; Tabor and Richardson, 1989b, *Proc.Natl.Acad.Sci. USA*, 86:4076-4080; U.S. Pat. No. 5,821,058) or the so-called transcriptional sequencing (TS) method described in U.S. Pat. No. 6,074,824, were not operable as such for base sequencing of a nucleic acid template comprising at least one base different from the standard W-C bases according to the present invention since terminators for bases different from W-C bases where not available in the art.

The inventor of the present invention has therefore developed new and improved methods for the determination of the nucleotide base sequence of nucleic acid templates comprising at least one base capable of base pairing and different from standard Watson-Crick (W-C) bases. According to one embodiment, the method comprises:

A) providing a nucleic acid template comprising at least one base capable of base pairing and different from the standard W-C bases;

B) elongating said template using a primer or a promoter or a promoter and an initiator in the presence of a nucleic acid synthesizing enzyme, nucleic acid synthesizing enzyme substrates and substrate derivatives;

C) determining the base sequence of the elongation product obtained in B).

According to one realization, the product of step B) can comprise a plurality of polynucleotides and each of said polynucleotides is separated from the others differing in length by a single nucleotide, and the nucleic acid sequence is determined according to method described in U.S. Pat. No. 5,821,058.

According to another realization, after step A) an annealing reaction between said template and a primer able to hybridize to said template is carried out.

The nucleic acid template according to step A) preferably comprises at least one standard W-C base A, C, G, T or U and at least one base capable of base pairing and different from the standard W-C bases. The nucleoside triphosphates having bases different from the standard W-C bases can be provided at the same concentration as those having the standard W-C bases. According to the nucleoside triphosphates having bases different from the standard W-C bases that are used, the nucleoside triphosphate concentration between the two kinds of bases can be different. When isoC and isoG are added, for instance, the concentrations of isoC and isoG triphosphates are lower than the concentration of the nucleoside triphosphates having the standard W-C bases.

The base different from the standard W-C bases can be any base capable of base pairing. It can be a non-standard W-C bases as defined in Benner, S. A. U.S. Pat. No. 5,432,272, for example isoG and/or isoC (Roberts et al., 1995, *Tetrahedron Letters*, Vol.36, No.21, pp.3601-3604, Elsevier Science Ltd), or can be a non-W-C base (neither standard nor non-standard) and capable of hydrophobic base pairing.

Examples of non-standard W-C bases are iso-C; iso-G; 2,6-diaminopyrimidine; xanthine; 6-amino-5-substituted pyrazin-2(1H)-one;
1-methyl-pyrazolo[4,3-d]pyrimidine-5,7(4H,6H)-dione;
5-aza-7-deazaguanine;
6-amino-3-substituted pyrazin-2(1H)-one;
3-amino-l-methylpurin-2-one;2,4-diamino-5,6-dihydropyrimidine;
2-amino-6-(N,N-dimethylamino)purine; pyridin-2-one;
other heterocyclic bases selected from the group consisting of the structural formulae of FIG. 3. In particular, the bases 2-amino-6-(N,N-dimethylamino)purine and pyridin-2-one are disclosed in Ishikawa, M. et al., 1999, *Nucleic Acids Symp Ser,* 42:125-126.

Examples of non-W-C bases (for instance exhibiting hydrophobic base pairing) are 3-methyl isocarbostyril; 5-methyl isocarbostyril; 7-propynyl isocarbostyril; m-xylene; 1,3,4-trimethylbenzene; 2-methylanaphthalene; 1,4-dimethylnaphthalene; 1-methylanaphthalene; naphthalene; 7-azaindole; isocarbostyril; 6-methyl-7-asaindole; 3-propynyl-7-azaindole; imidazopyridine; pyrrolopyridine. In particular, the base 7-propynyl isocarbostyril, which is capable of pairing with itself is described by Robert F. Service in *Science,* July 2000, Vol.289:232-235.

According to a particular realization, when the template is DNA, the synthesizing enzyme is a DNA-dependent DNA polymerase, the synthesizing enzyme substrate are dNTPs and substrate derivatives comprise ddNTPs.

Examples of DNA-dependent DNA polymerases are *E. coli* DNA poll Kelenow fragment (Sambrook, J. et al., 1989, *Molecular Cloning: A Laboratory Manual*; Ausubel, F. M. et al. Eds., 1989, In *"Short Protocols in Molecular Biology,"* pp.201-231. Wiley, N.Y.); modified T7 DNA pol (Sequenase) (Tabor, S. et al., 1987, *Proc. Natl. Acad. Sci. USA* 84:4767-4771); and thermostable polymerases Taq, Tbr, Tfl, etc.) (Eun, H-M., 1996, Enzymology Primer for Recombinant DNA Technology, 1996 Academic Press).

Preferably, a dNTP or ddNTP used is labeled. According to a further particular embodiment, the primer or initiator of step B) is labeled. The label can be an isotope, chromophore or fluorophore label.

According to another particular realization, when the template is DNA, the synthesizing enzyme is a DNA-dependent RNA polymerase, the synthesizing enzyme substrates are NTP and substrate derivatives comprise 3'-dNTP derivatives.

Examples of DNA-dependent RNA polymerases are T7, T3 and SP polymerases (Axelrod, V. D. et al., 1985, *Biochem.* 24:5716-5723; Parvin, J. D. et al., 1986, *DNA* 5:167-171).

The NTPs or 3'-dNTP derivative can be labeled. Preferably, the primer or initiator of step B) is labeled. The label can be a radioactive isotope, chromophore or fluorophore.

According to a further realization, when the template is RNA, the synthesizing enzyme is a RNA-dependent DNA polymerase, the synthesizing enzyme substrate is dNTP and substrate derivatives comprise ddNTPs.

Examples of RNA-dependent DNA polymerases are AMV and MoLV polymerases (Karanthanasis, S., 1982, *Focus BRL,* 4:6-7; Geliebter, J., 1989, *Focus (BRL),* 9:5-8; Hahn, C. S., et al., 1989, *Method Enzymol.,* 180:121-130).

The dNTP or ddNTP can be labeled. Preferably, the primer or initiator of step B) is labeled. The label can be an isotope, chromophore or fluorophore.

Further, when the template is RNA and the synthesizing enzyme is a RNA-dependent RNA polymerase, the synthesizing enzyme substrate is NTP and substrate derivatives are 3'-dNTPs derivatives.

An example of a RNA-dependent RNA polymerases is for example Qβ replicase (Kramer, F. R., 1978, *Proc. Natl. Acad. Sci. USA,* 75:5334-5338).

The NTP or 3'-dNTP derivative can be labeled. The primer or initiator of step B) can also be labeled. The label can be a radioactive isotope, chromophore or fluorophore.

The bases capable of base pairing and different from the standard W-C bases are preferably as described above.

An example of a non-standard W-C base capable of base pairing and different from the standard W-C standard bases is isoC and/or isoG.

2',3'-dideoxyisoguanosine 5'-triphosphate (ddisoG) and 2',3'-dideoxyisocytidine 5'-triphosphate (ddisoC) can be used as terminators in a process according to the present invention when isoG and/or isoC are used as substrate derivatives.

Accordingly, the present invention also provides new methods for the preparation of the compounds 2',3'-dideoxyisoguanosine 5'-triphosphate (ddisoG) and 2',3'-di deoxyisocytidine 5'-triphosphate (ddisoC).

The determination of the base sequence of nucleic acid templates according to the invention comprising at least one base capable of base pairing and different from the standard Watson-Crick (W-C) bases, can also be performed by using MALDI-TOF-MS analysis (U.S. Pat. No. 5,691,141)

Accordingly, the present invention also discloses a method for the determination of the base sequence of nucleic acid templates according to the invention comprising:

A) providing a nucleic acid template comprising at least one base capable of base pairing and different from the standard W-C bases;

B) elongating said template using a primer or a promoter or a promoter and initiator in the presence of a nucleic acid synthesizing enzyme, nucleic acid synthesizing enzyme substrates and substrate derivatives;

C) determining the base sequence of the elongation product obtained in B) by determining the mass of fragmentation products using MALDI-TOF-MS analysis.

According to another embodiment, a method for determining the nucleotide base sequence of nucleic acid template comprising at least one base capable of base pairing and different from standard W-C bases can also be performed based on the chemical degradation method (Maxam-Gilbert method or improvements thereof). This method can be performed starting by chemical modification at only one end of a single strand template (Maxam and Gilbert, 1980, *Methods Enzymol,* 65:499-559; also Sambrook et al., 1989, Chapter 13.3), or by chemical modification of both ends of a double strand template (Maxam-Gilbert method (Maxam and Gilbert, 1977, *Proc.NatlAcad.Sci. USA,* 74:560-564).

A double strand template can be prepared from the single strand template of the invention according to standard techniques known in the art. For instance, a single strand template comprising at least one base different from W-C base is prepared, then a complementary strand is prepared by PCR amplification, using at least a PCR primer comprising a specific restriction enzymatic site (for instance FokI). The double strand template obtained from amplification is then cleaved using the specific restriction enzyme (for instance FokI: Toyobo Biochemical Catalogue) and the fragment obtained is chemically modified at both ends and sequenced by chemical degradation Accordingly, it is provided a method for determining the nucleotide base sequence of nucleic acid templates comprising at least one base capable of base pairing and different from standard Watson-Crick (W-C) bases, wherein standard W-C bases are A, C, G, T or U, comprising:

1) providing a nucleic acid template comprising at least one base capable of base pairing and different from the standard W-C bases;
2) labeling one end of said template;
3) chemically degrading said labeled template;
4) determining the base sequence of the product obtained in 3).

Preferably, in the method above, the nucleic acid template comprises at least one standard W-C base A, C, G, T or U and at least one base capable of base pairing and different from the standard W-C bases.

The bases capable of base pairing and different from the standard W-C bases are preferably as described above.

An example of a non-standard W-C base capable of base pairing and different from the standard W-C standard bases is isoC and/or isoG.

The determination of the base sequence of nucleic acid templates according to the invention comprising at least one base capable of base pairing and different from the standard Watson-Crick (W-C) bases can also be performed by using other technologies known in the art like, for example, pyrosequencing (real-time pyrophosphate DNA sequencing method) (Ronaghi, M. et al. *Anal. Biochem.* 242 (1996) 84-89; Ronaghi, M. et al. *Science* 281 (1998) 363-365), or array methods based on sequencing by hybridization (Drmanac, I. et al. *Genomics* 4,1989, 114-128; also U.S. Pat. No. 5,202,231).

Accordingly, the present invention discloses a method (pyrosequencing) for the determination of the base sequence of a nucleic acid template according to the invention comprising:

a) providing a nucleic acid template comprising at least one base capable of base pairing and different from the standard W-C bases;
b) carrying out elongation by using a primer, a promoter, or a promoter and initiator in the presence of nucleoside triphosphates whose base comprises at least one base capable of base pairing and different from the standard W-C bases, by adding a first nucleoside triphosphate and detecting PPi release and degrading the first nucleoside triphosphate, then adding a second nucleoside triphosphate and detecting PPi and degrading the second nucleoside triphosphate, and repeating the procedure according to the kind of base of the nucleoside triphosphates provided;
c) repeating the step above according to the template bases number desired to be sequenced;
d) determining the sequence of the template as the reverse complement of the sequence of added nucleoside triphophates;

The present invention also provides a method (hybridization sequencing) for the determination of the base sequence of a nucleic acid template according to the invention comprising:

a) providing short (preferably 4-12 mer) oligonucleotides fixed on a chip, these oligonucleotides comprising at least one base capable of base pairing and different from the standard W-C bases and having overlapping frames displaced by one or two bases;
b) hybridizing these oligonucleotides with a labeled template comprising at least one base capable of base pairing and different from the standard W-C bases;
c) detecting the signal of the label;
d) determining the sequence of the template by determining the set of overlapping oligonucleotides hybridizing to the labeled template.

The conditions for performing the hybridization sequencing are-described in Drmanac, I. et al. *Genomics* 4,1989, 114-128 and also U.S. Pat. No. 5,202,231.

The present invention will be further explained in more detail with reference to the following examples.

EXAMPLE 1

Preparation of 2',3'-dideoxyisozuanosine 5'-triphosphate (ddisoG)

Hydrogen peroxide (30%, 3.5 ml) was added to a solution of sodium carbonate (2.6 g, 25 mmol) in water (25 ml). Maleic anhydride (2.45 g, 25 mmol) was then added, and the mixture was stirred at 0° C. for 30 min, at which point all of the maleic acid was dissolved. Concentrated sulfuric acid (1.5 ml) in water (7.0 ml) was then added at 0° C. The mixture was extracted with ether (8×25 ml), and the combined extracts were stored at 0° C.

A solution of monopermaleic acid in water was obtained by evaporating 0.31 ml of the ether extracts in the presence of water (36 µl) in a stream of air. The pH of the solution was adjusted to 7.0 with NaOH (1 M), and a solution of disodium salt of ddATP (5 mg, 10 µmol, ICN, in 18 µl of water) was added. The reaction mixture was stirred for 24 h at room temperature, and the pH was adjusted to 4.5 with HCl (1 M). EtOH (absolute, 545 µl) was added, and the resulting precipitate was recovered by centrifugation and dissolved in water (2.0 ml), the pH adjusted to 4.5, and the N-oxide of ddATP was obtained by precipitation with ether (3.6 mg, 73%).

The N-oxide of ddATP (3.6 mg, 7.3 µmol) was dissolved in water (4.5 ml), and the solution was placed in a photochemical reaction tube. The mixture was irradiated for 2 h with light from a high pressure mercury arc lamp, the pH adjusted to 10 (28% aqueous ammonia solution), and the mixture was stirred at room temperature overnight.

Water was removed in vacuo, and the material was purified by HPLC (YMC ODS 120A semi-preparative column, eluted with 20 mM of aqueous triethylammonium acetate solution over 60 min in a gradient of 0.2 to 8% acetonitrile).

Fractions containing product were collected, and the buffer was recovered in vacuo yielding 2',3'-dideoxyisoguanosine 5'-triphosphate.

Preparation of 2',3'-dideoxyisocytidine 5'-triphosphate (ddisoC)

Diethyl azodicarboxylate (40% in Toluene, 1 ml, 2 mmol) was added to a mixture of 2',3'-dideoxyuridine (100 mg, 0.47 mmol) and triphenylphosphine (0.26 g, 1 mmol) suspended in tetrahydrofuran (1 ml). The mixture was stirred at room temperature overnight, and the resulting pale yellow suspension containing 2,5'-anhydro-2',3'-dideoxyuridine was used for the next reaction without purification.

Methanol (15 ml) was saturated with dry ammonia at 0° C., and the yellow suspension of 2,5'-anhydro-2',3'-dideoxyuridine was added. The mixture was stirred at room temperature for three days. TLC (silica gel, 20% methanol/dichloromethane) showed essentially complete conversion.

Stirring was continued for an additional five days, the solvents were removed by evaporation. The resulting residue was extracted with water (5×2 ml).

2',3'-deoxyisocytidine was obtained by evaporation of the solvent (48 mg, 48%).

A solution of 2',3'-deoxyisocytidine (48 mg, 0.2 mmol) in trimethyl phosphate (0.822 ml) at 0° C. was treated with phosphoryl chloride (0.039 ml) and stirred for 1.5 h. To the mixture was then rapidly added a solution of tris(tributylammonium) pyrophosphate (1.2 mg) in dimethylformamide (2.5 ml). The mixture was agitated vigorously for 1 min.

A solution of triethylammonium bicarbonate (1 M, pH 8.0, 2 ml) was then added. The solvents were removed by evaporation, and the product was purified by HPLC (YMC ODS 120A semipreparative column, eluted with 20 mM of aqueous triethylammonium acetate solution over 60 min in a gradient of 0.2 to 8% acetonitrile).

EXAMPLE 2

Sequencing of oligonucleotide 20 pmol of the reverse 3' primer, REV-4: 5'-AGC GGA TAA CAA TTT CAC AC-3' (SEQ ID NO:1)(synthesized with an EXPEDITE 8909 automatic synthesizer according to the standard protocol), was labeled using a MEGALABEL oligonucleotide labeling kit (Code No. 6070, Takara, Japan) and [gamma-32P] ATP (Code No. AA0018, 6000Ci/mmol, Amersham Pharmacia Biotech, USA).

1.5 pmol of labeled primer prepared above and 0.75 pmol of an oligonucleotide template, PCR4-1:5'-CAC GAC GTT GTA AAA CGA CGG CCA GTG TTA CGg cAT TGC cgA TGA CGA TGG TGT GAA ATT GTT ATC CGC T-3' (SEQ ID NO:2) (synthesized using an EXPEDITE 8909 synthesizer according to the standard protocol), and 2.25 µl of 10× Klenow buffer (Code No. 6015A, Takara, Japan) was mixed and the mixture volume adjusted to 18 µl. The mixture was incubated at 95° C. for 5 min, and put on ice. Three µl of water and 1.5 µl of 2unit/µl Klenow fragment were added to produce the annealing mixture.

2 µl of termination mixture, dddA (416.7 µM dATP, 83.3 µM dCTP, 83.3 µM dGTP, 83.3 µM dTTP, 40 µM diGTP, 40 µM diCTP, 100 µM ddATP, 16.7 mM Tris-HCl, pH 7.5, 166.7 µM EDTA), dddC (83.3 µM dATP, 416.7 nM dCTP, 83.3 µM dGTP, 83.3 µM dTTP, 40 µM diGTP, 40 µM diCTP, 50 µM ddCTP, 16.7 mM Tris-HCl, pH 7.5, 166.7 µM EDTA), dddG (83.3 µM dATP, 83.3 µM dCTP, 416.7 nM dGTP, 83.3 µM dTTP, 40 µM diGTP, 40 µM diCTP, 58.3 µM ddGTP, 16.7 mM Tris-HCl, pH 7.5, 166.7 µM EDTA), dddT (83.3 µM dATP, 83.3 µM dCTP, 83.3 µM dGTP, 416.7 nM dTTP, 40 µM diGTP, 40 µM diCTP, 200 µM ddTTP, 16.7 mM Tris-HCl, pH 7.5, 166.7 µM EDTA), dddiG (83.3 µM dATP, 83.3 µM dCTP, 83.3 µM dGTP, 83.3 µM dTTP, 416.7 nM diGTP, 40 µM diCTP, 100 µM ddTTP, 16:7 mM Tris-HCl, pH 7.5, 166.7 µM EDTA), dddiC (83.3 µM dAT, 83.3 µM dCTP, 83.3 µM dGTP, 83.3 µM dTTP, 40 µM diGTP, 416.7 nM diCTP, 100 µM ddTTP, 16.7 mM Tris-HCl, pH 7.5, 166.7 µM EDTA), was dispensed in 500 µl microtube.

3.5 µl of the annealing mixture was dispensed in each of the 6 tubes containing a different termination mixture. Each mixture was incubated at 37° C. for 20 min. 4 µl of stop solution (95% formamide, 0.05% bromophenol blue, 0.05% xylene cyanol FF) was dispensed in each tube and incubated at 95° C. for 3 min. After incubation, each tube was put on ice.

2 µl of each mixture was applied on 20% polyacrylamide gel (20% T, 5%C, wherein T is acrylamide+bis-acrylamide, while C is bis-acrylamide) containing 7M urea with TBE buffer (88.9 mM Tris-borate, pH 8.3, 2.5 mM EDTA). Electrophoresis was carried out at 45 W constant power for 4 hrs.

After electrophoresis, the gel was fixed with 10% methanol and 10% acetic acid, for 15 min. The fixed gel was transferred to paper (3MM Chr, Whatman, UK), covered with wrapping film "Saran wrap" (Asahi Chemical Industries Co., Japan), and dried at 80° C. for 1 hr under vacuum.

The dried gel was exposed on a BAS imaging plate (Fuji film, Japan) for 1 hr, and then the image was detected using a BAS 2000 imaging analyzer (Fuji film, Japan).

In the experiment reported in FIG. 1, it is shown that when isoG and isoC are used as substrates, when the concentrations of isoG and isoC as substrates are lower than the concentration of A, C, G, T, the sequence of the nucleic acid is legible. When instead the concentrations of isoC and isoG were the same that of A, C, G, T, the nucleic acid sequence could not be determined. However, when bases different from isoG and isoC (and from A, C, G, T or U) a substrate concentration the same, lower or higher than the A, C, G, T or U concentration can be used.

The sequence shown in FIG. 1B), limited to the sequence comprising the included isoG and isoC bases (indicated as lower "g" and "c" letters in the sequence, and "iG" and "iC" in the Figure), is TTCACACCATCGTCATcgGCAATgcCG (SEQ ID NO:3).

EXAMPLE 3

Protein binding assays

The following experiment has been performed according to the SELEX protocol described in detail in Tuerk & Gold, 1990, *Science,* 249:505; Tuerk et al., 1992, *Proc. Acad. Sci. USA* 89:6988. In this experiment, the SELEX protocol was performed in a similar manner as for single stranded DNA.

Preparation of target protein

A hypothetical protein from the RIKEN mouse full-length cDNA clone bank (http://genome.rtc.riken.go.ip/) was chosen as the target protein. The cDNA sequence of the selected clone is reported in SEQ ID NO:4. The open reading frame (ORF) is from bases 300-935. The sequence of the encoded protein (corresponding to the ORF) is reported in SEQ ID NO:5.

The ORF was amplified by PCR with the primers 5'-GTG CCC ACC TCC TCG GCA TAT GCC C-3' (SEQ ID NO:6) and 5'-TGA AGT TTC CAA TGG GAT CCT ATA AC-3' (SEQ ID NO:7). The amplified product was digested with NdeI and BamHI. The digested DNA was ligated into the corresponding sites of the vector pET16b (Novagen, 69662-3, USA). The recombinant plasmid was introduced into *Escherichia coli* BL21(DE3). The transformant was cultivated in LB medium containing 100 µg/ml of ampicillin. When the optical density at 600 nm reached 1.0, 100 mM isopropyl-β-D-thio-galactoside (IPTG) was added to the final concentration of 0.4 mM. After cultivation for 3 hrs, the *E. coli* cells were collected by centrifugation at 5,000×g for 5 min at 4° C. The harvested cells were resuspended in 20 mM phosphate buffer (pH 7.4), sonicated, and centrifuged at 15,000×g for 30 min at 4° C. The supernatant was applied to a nickel-chelate column (HisTrap kit, Code No. 17-1880-01 Amersham Pharmacia Biotech, USA). The absorbed protein was eluted with 300 mM imidazole. The purity of the expressed protein was tested by SDS-PAGE. The yield of expressed and purified protein was 50 µg/l culture.

Preparation of random single stranded DNA pool

A random template pool of single stranded DNA that consists of a 40 nucleotide random region (defined as [N40]) flanked by a left flanking region 5'-TGT AAA ACG ACG GCC AGT-3' (SEQ ID NO:8) and by a right flanking region 5'-GT GTG AAA TTG TTA TCC GCT-3' (SEQ ID NO:9) was synthesized using an automated DNA synthesizer (EXPEDITE 8909 using the standard protocol).

The random template pool of single stranded DNA is therefore defined in this way:

5'TGT AAA ACG ACG GCC AGT-[N40]-GT GTG AAA TTG TTA TCC GCT3'.

The random pool region [N40] was generated by reacting with all six types of phosphoramidites (that is A, T, C, G, isoC and isoG) at the fixed concentrations of 5%(w/w) in acetonitrile 95%.

Defined nucleotide sequence primers (SEQ ID NO:1 and SEQ ID NO:10) for the flanking regions of [N40] of the template pool served as primer annealing sites for PCR. The complexity of the template pool was estimated as in the order of $10^{14}$ molecules. After the synthesis, the template pool was amplified by PCR with the corresponding primers 5'-AGC GGA TAA CAA TTT CAC AC (SEQ ID NO:1) and 5'-TGT AAA ACG ACG GCC AGT-3' (SEQ ID NO:10) under standard PCR conditions except the concentration of isoG and isoC (100 µM each) corresponded to one-half of the concentration of the other dNTPs (dATP, dTTP, dCTP and dGTP) (200 µM each for A, C, G, T). The above obtained DNA was used for a second PCR, without adding the 3' primer and, a single stranded DNA was generated. 1 µM oligonucleotide having the sequence 5'-GT GTG AAA TTG TTA TCC GCT-3' (SEQ ID NO:11) which was complement of the 3' primer, was added to inactivate the remaining 3' primer and maximize the fraction of DNA synthesis producing random single stranded DNA resulting from extension of the 5' primer.

Binding assay

The single stranded DNA pool (200pM) prepared above was incubated with the protein (obtained in the preparation of target protein above) in a binding buffer of PBS (10 mM $Na_2HPO_4$, 1.8 mM KH2PO4, 130 mM NaCl and 2.7 m MKCl, pH7.4) containing 0.01% human serum albumin (SIGMA, product No. A1653) and 1 mM $MgCl_2$. The mixture of the protein and the random single stranded DNA pool was incubated at 4° C. overnight, and then incubated at 37° C. for 15 minutes. Then the obtained protein-DNA complex was separated from the unbound DNA and protein species by nitrocellulose filter partitioning methods as described in Jellinek et al., 1994, *Biochemistry*, 33:10450-10456. Nitrocellulose filters (Millipore, 0.4 µm pore size, type HA) were washed with 5 ml PBS buffer before using for selection. The mixture of the protein and the random single stranded DNA pool was applied to the filters under gentle vacuum in 45 µl aliquot and washed with 5 ml PBS. The selected single stranded DNA bound to the protein was then extracted from the filters, separated from the protein (according to Jellinek et al., 1994) and amplified again by the PCR methods described above. This cycle was repeated 20 rounds. The selected single stranded DNA, which is indicated as Template 1, comprises an oligonucleotide aptamer sequence. It was sequenced according to the method described in Example 2. The sequence of Template 1 is 5' TGT AAA ACG ACG GCC AGT GCG TAA CgG GGT cTA TGT TCC CGC ACA CcG TGG CAA AAC TGT GTG AAA TTG TTA TCC GCT 3' (SEQ ID NO:12). The sequence of the aptamer portion is 5'-GCG TAA CgG GGT cTA TGT TCC CGC ACA CcG TGG CAA AAC T-3' (SEQ ID NO:13).

EXAMPLE 4

Aptamer Chip analysis

Aptamer preparation

Template 1 (SEQ ID NO:12) comprising the aptamer (SEQ ID NO:13) selected and sequenced in Example 3, was amplified by a standard PCR method with a primer having SEQ ID NO:10 and a primer 5'-TGC CAT TTC ATT ACC TCT TTC TCC GCA CCC GAC ATA GAT GAC ACT ACT ACG GTA TGA TCC TAT GGA GAA CGC TCA GCG GAT AAC AAT TTC ACA C-3' (SEQ ID NO:14) which comprises the recognition site of Pl-SceI, a spacer of 50 bp 5'-GCA CCC GAC ATA GAT GAC ACT ACT ACG GTA TGA TCC TAT GGA GAA CGC TC-3' (SEQ ID NO:15), and the annealing site to single stranded DNA 5'-A GGG GAT AAC AAT TTC ACA C-3' (SEQ ID NO:16), and in the standard condition (200 µM for A, C, G, T) except for the concentrations of isoG and isoC which were 100 µM.

The purpose of the spacer sequence was to bind the aptamer sequence to a chip substrate.

After PCR, the obtained double stranded DNA comprising the aptamer (this double stranded DNA being defined Template 2) was incubated at 37° C. for 30 minutes with Pl-SceI (New England BioLabs) to create an overhanging 3' end.

Preparation of aptamer chip

An amino group was introduced into the 3' end of the synthesized Template 2 (double stranded DNA) as follows.

1 µg of the above Template 2 was incubated at 37° C. for 1 hour with 50 units of terminal deoxynucleotidyl transferase (TdT)(TOYOBO Japan) in 50 µl TdT buffer containing 0.5M 2', 3'-deoxy-5-(3-aminopropynyl)UTP, and the DNA was collected by ethanol (EtOH) precipitation by using for 1 volume of reaction mixture 1/10 volume of 3M $CH_3COONa$ and 2.5 volumes of EtOH.

The substrate of the aptamer chip was made from a glass slide (S12E 3×1", 0.93 to 1.05 mm). The slide was immersed in 100% trifluoroacetate at room temperature for 1 hour and dried. Then it was immersed again in 2%(v/v) aminopropyltriethoxysilane and 50% (v/v) acetone at room temperature for 24 hours following by washing with 50% (v/v) acetone three times and with 100% acetonitrile one time and then dried.

0.5 µg of Template 2 (double stranded DNA) with the amino group at 3' end and succinic anhydride at the final concentration of 5% were allowed to react in a volume of 10 µl to introduce a carboxy group to the 3' end of the DNA. This solution was mixed and immediately used for ligation to a slide glass.

Template 2 with the carboxylated 3' end was fixed on the aminated glass slide as follows. Template 2 with carboxylated 3' end was mixed with carbodiimide at a final concentration of 5% and 0.4 µl of the mixture was dotted with a micropipette on the aminated glass slide. The glass slide was then incubated at 50° C. for 6 hours, and washed with a solution of 10 mM Tris-Cl [pH8.0], 1 mM EDTA, 0.1%

SDS, and 0.1M NaOH followed by washing with a solution of 10 mM Tris-HCl [pH8.0], and 1 mM EDTA. Thus, the glass slide on which single stranded DNA was fixed was obtained. It consists of a single stranded DNA comprising a primer sequence, the aptamer and the spacer. The DNA is fixed on the chip substrate by the spacer sequence.

Detection of target proteins in human serum

The glass slide (3×1", 0.93 to 1.05 mm) on which single stranded DNA is fixed (aptamer glass prepared above) was pre-treated by incubating in PBS containing 3% gelatin (Bio-Rad) at 37° C. for 10 min, and maintained in PBS solution. Human serum (SIGMA, products No. S7023) was diluted (to 0.1 mg protein/ml) with PBS, and labeled with $^{125}$I-IODOGEN (Pierce) to a specific activity of 70 mCi/mg protein. 0.5 ml solution of $^{125}$I-labeled serum protein was put on the aptamer glass which was pretreated with PBS containing gelatin, and incubated at 37° C. for 30 min. The aptamer glass was then washed gently 10 times with fresh PBS containing 3% gelatin (Bio-Rad) at room temperature. The radioactivity on the aptamer glass was detected by a conventional autoradiographic method.

Figure 2:
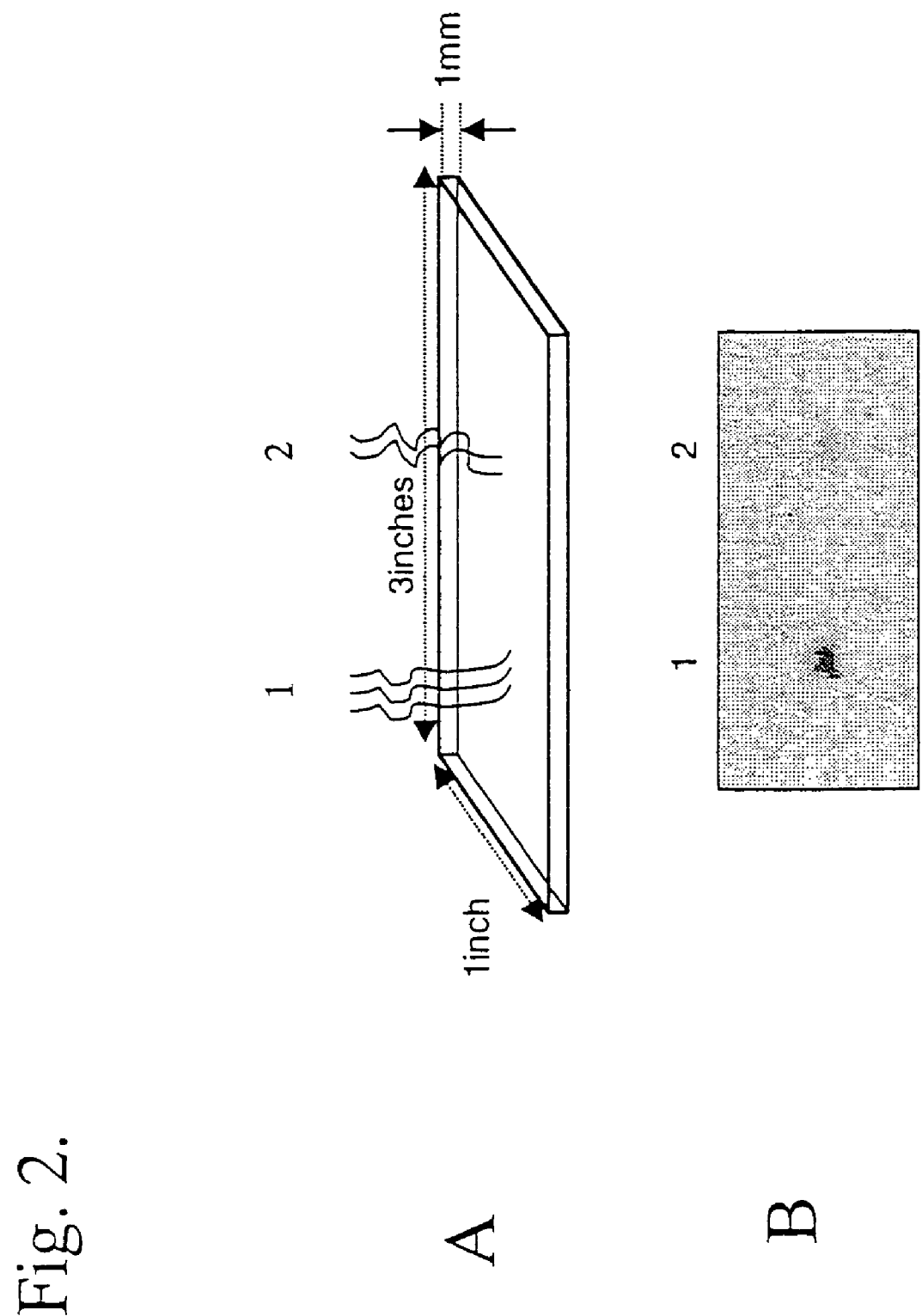
FIG. 2 relates to the detection of a ligand protein in human serum using an aptamer chip as disclosed in Example 4. A) refers to the aptamer chip glass. A specific aptamer for the ligand protein having a base sequence disclosed in SEQ ID NO:4 and a negative control aptamer (SEQ ID NO:15) were fixed at locations 1 and 2, respectively. B) shows an autoradiogram of aptamer chip glass A after treatment with $^{125}$I-labeled human proteins.

FIG. 2 shows the detection of a ligand protein in human serum using the aptamer chip as disclosed in this Example 4. A) refers to the aptamer chip glass. A specific aptamer for the ligand protein having a base sequence disclosed in SEQ ID NO:4 and a negative control aptamer 5'-TGT AAA ACG ACG GCC AGT TTC CgG AGT CAC gGC TGC GGG cCG TCT GAG CCG TTT GCA CGT GTG AAA TTG TTA TCC GCT -3' (SEQ ID NO:17) were fixed at locations 1 and 2, respectively. B) shows an autoradiogram for aptamer chip glass A after treatment with $^{125}$I-labeled human proteins.

EXAMPLE 5

Sequencing of oligonucleotide using 6 fluorescent dyes

Six labeled with fluorescent dyes primers were prepared for sequencing. Four fluorescent dye primers were commercial products (sold as a set of four dyes), BODIPY dye M13 forward primer(catalog number: 5016-FPW, SeqWright Inc., US; Metzker, M. L., Lu, J., Gibbs, R. A.: Electrophoretically Uniform Fluorescent Dyes for Automated DNA Sequencing. Science, 271, 1420-1422, 1996). The other two fluorescent dye M13 forward primers were obtained from Genset: one was BODIPY-630/650 (absorption maxima: 625 nm, emission maxima: 640 nm) and the another was BODIPY-TR (absorption maxima: 589 nm, emission maxima: 617 nm). These two fluorescent dye M13 primers comprised the BODIPY-630/650 or the BODIPY-TR dye (produced by Molecular Probes Inc.) attached to the 5'-end of the M13 forward primer having the sequence 5'-GTA AAA CGA CGG CCA GT-3' (SEQ ID NO:18) (produced by Genset). Six micro tubes (MicroAmp Reaction tubes, catalog number N801-0533, Applied Biosystems) were prepared for dye primer sequencing reactions. In each tube, 2 μl of a mixture comprising 0.125 pmol of each fluorescent dye primer, 40 fmol of an oligonucleotide template 5-CTATGACCATG-gTcTCGCCTTGgTcTTTAGGTGACAC-TATTTACTGGCCGTCGT TTTAC-3' (SEQ ID NO:19) ["g" indicates diGTP, (deoxy isoGTP) and "c" indicates diCTP (deoxy isoCTP)] synthesized using an EXPEDITE 8909 automatic synthesizer according to the standard protocol, and water were mixed with 2 μl of reaction mixture (1U Thermo Sequenase DNA polymerase; 150 μU *Thermoplasma acidophilum* inorganic pyrophosphatase; 20 mM Tris-HCl, pH 8.5, 1 mM dithiothreitol, 100 mM KCl, 0.1 mM EDTA, 0.5% Tween-20, 0.5% Nonidet P-40, 50% glycerol, 65 mM MgCl$_2$ ) and with 4 μl of each termination mixture to form a final mixture of 8 μl. The contents of the termination mixtures were:

d/ddA mixture: 30 μM dATP, 150 μM dCTP, 150 μM dGTP, 150 μM dTTP, 150 μM diGTP, 150 μM diCTP, 150 μM ddATP;

d/ddC mixture: 150 μM dATP, 30 μM dCTP, 150 μM dGTP, 150 μM dTTP, 150 μM diGTP, 150 μM diCTP, 150 μM ddCTP;

d/ddG mixture: 150 μM dATP, 150 μM dCTP, 30 μM dGTP, 150 μM dTTP, 150 μM diGTP, 150 μM diCTP, 150 μM ddGTP;

d/ddT mixture: 150 μM dATP, 150 μM dCTP, 150 μM dGTP, 30 μM dTTP, 150 μM diGTP, 150 μM diCTP, 150 μM ddTTP;

d/ddiG mixture: 150 μM dATP, 150 μM dCTP, 150 μM dGTP, 150 μM dTTP, 30 μM diGTP, 150 μM diCTP, 150 μM ddisoGTP;

d/ddiC mixture: 150 μM dATP, 150 μM dCTP, 150 μM dGTP, 150 μM dTTP, 150 μM diGTP, 30 μM diCTP, 150 μM ddisoCTP;

The final mixture of each tube was reacted using a thermal cycler (DNA Engine Tetrad thermal cycler, which is a thermal cycler having 4 independent thermal cycling blocks, and is a trade name of M J Research Inc. US) according to the standard protocol for Thermo Sequenase DNA polymerase (Amersham Pharmacia Biotech Ltd.). A description of the use of the cycle sequencing program of DNA Engine Tetrad for Thermo Sequenase is disclosed in "Techniques of genome analysis in large-scale and gene functional analysis in the post-genome era", Hayashizaki et al., Publisher: Nakayama-shoten Co., Ltd, 2001, Japan. The reacted samples were transferred to 0.5 ml tubes (GeneAmp Thin-Walled Reaction tubes with Flat Caps, catalog number N801-0737, Applied Biosystems), then precipitated with EtOH according to the following procedure. 16 μl of 99% EtOH and 0.8 μl of 0.3M CH$_3$COONa solution were added to each tube and the tube was centrifuged at 15,000 rpm for 30 min. at 4° C. After removing the supernatant, 200 μl of 70% EtOH were added to each tube and the tube was centrifuged at 15,000 rpm for 10 min. at 4° C. After removing the supernatant, the tubes were left upside down for 5 minutes at room temperature in order to let water and EtOH evaporate. The samples were dissolved in 4 μl of water per tube and mixed. After drying up at 65° C., each sample was dissolved in 4 μl of 2 μM EDTA solution, transferred to a 96-well plate (catalog number 21971, Sorenson BioScience Inc.), incubated at 95° C. for 5 min, and put on ice.

Figure 4:
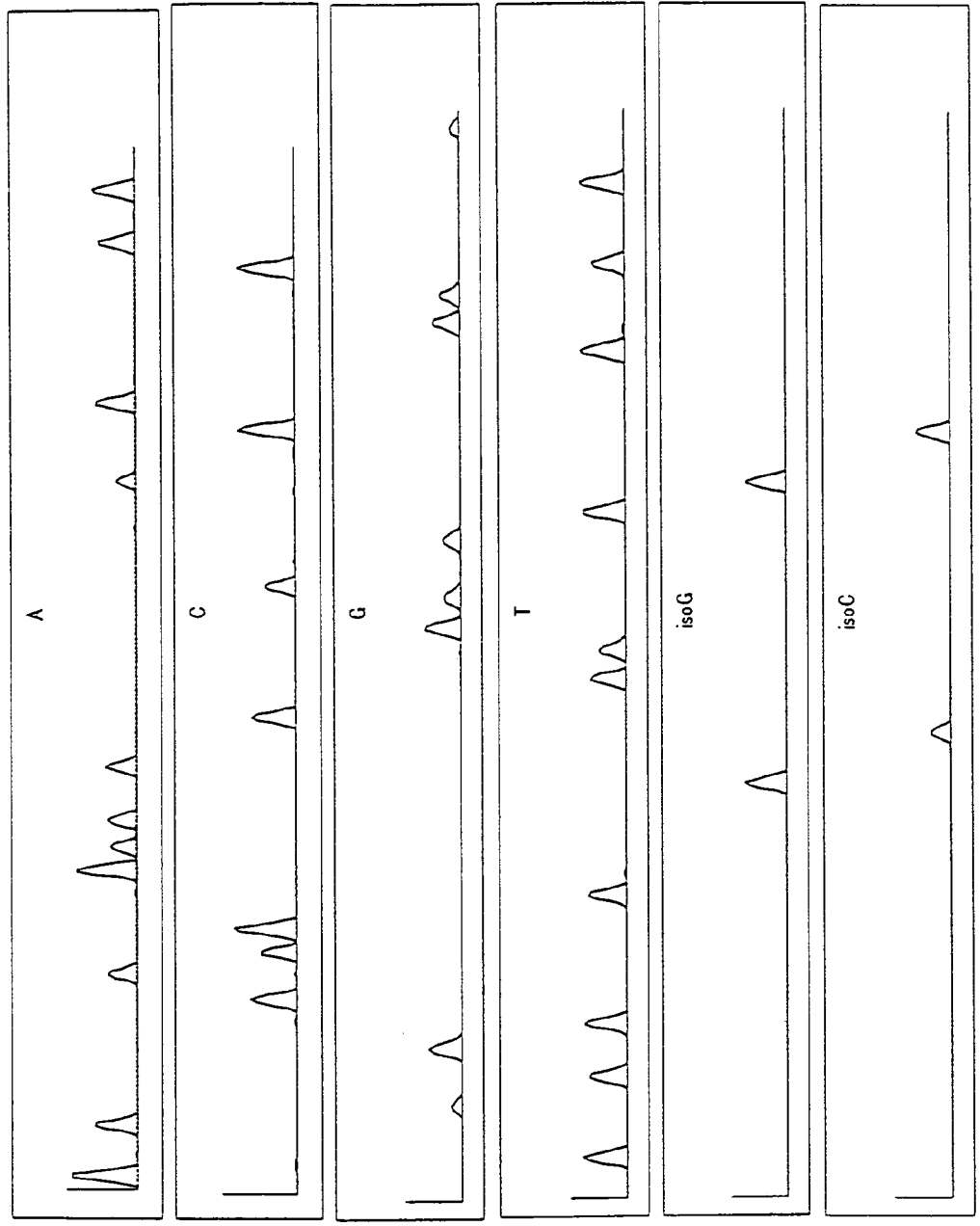
FIG. 4 shows the data from the individual electropherograms of the sequencing reactions in Example 5.
Figure 5:
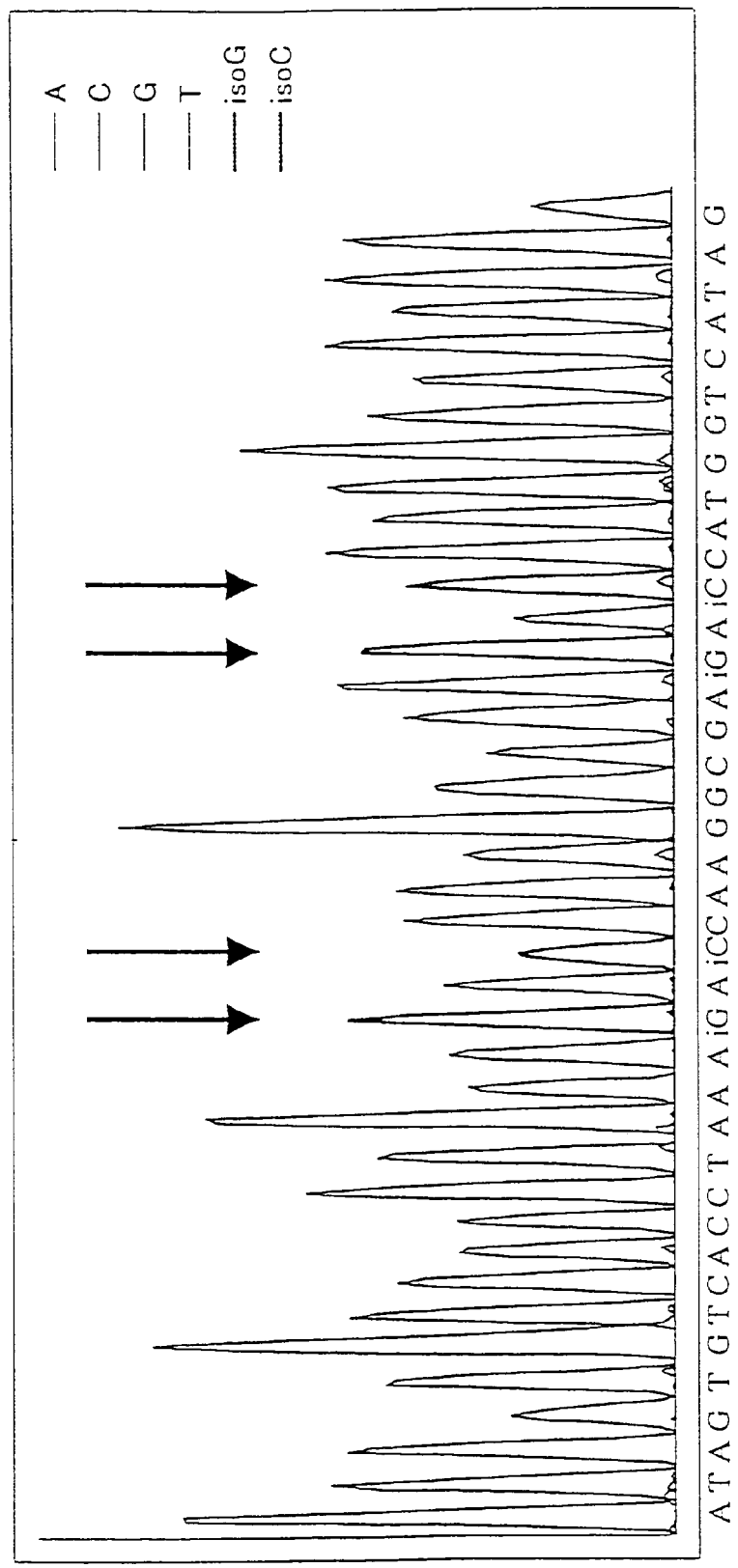
FIG. 5 shows the composite electropherogram obtained by combining the data in FIG. 4 to obtain the sequence of SEQ ID NO: 20.

Electrophoresis and fluorescence detection of reaction products were performed using the SCE 9610 Genetic analysis system (SpectraMedix Co. US) according to the manufacturer's procedure. After smoothing by using Fourier transformation and low pass filtration functions, background subtraction was performed for all data. For each 5 peak interval, a local minimum point, which value was minimum in the interval, was selected and lines connecting these points were assumed as a background signal of raw data. The 6 data sets were transformed linearly using a 6×6 matrix. This matrix was made in order to transform the 6 data which were obtained by electrophoresis of single dye, into one dominant datum and 5 quite minor data for each dye. Each of the obtained peaks was basecalled as a corresponding base (A,G,C,T,isoG, or isoC) (These techniques are described in Giddings M C, Brumley R L Jr, Haker M, Smith L M., "An adaptive, object oriented strategy for base calling in DNA sequence analysis," *Nucleic Acids Res.* 1993 Sep 25;21(19):4530-40.; Berno A J., "A graph theoretic approach to the analysis of DNA sequencing data". *Genome Res.* 1996 February;6(2):80-91). Electropherograms (that is a 6-channel chromatogram) of analyzed data are shown in FIGS. 4 and 5, in which the sequence reported is limited to the portion comprising the included isoG and isoC bases (indicated as lower "a" and "c" letters in the sequence, and "iG" and "iC" in the Figure). The sequence was ATAGTGTCAC-CTAAAgAcCAAGGCGAgAcCATGGTCATAG (SEQ ID NO:20).

Various articles of the scientific and patent literature are cited throughout this specification. Each such article is hereby incorporated by reference in its entirety and for all purposes by such citation.

The invention claimed is:

1. A method for determining the nucleotide base sequence of a nucleic acid template comprising at least one base capable of base pairing and different from the standard Watson-Crick (W-C) bases comprising:
   a) providing a nucleic acid template comprising at least one base capable of base pairing and different from the standard W-C bases;
   b) elongating said template using a primer or a promoter or a promoter and an initiator in the presence of a nucleic acid synthesizing enzyme, nucleic acid synthesizing enzyme substrates and nucleic acid enzyme substrate derivatives;
   c) determining the base sequence of the template as the reverse complement of the sequence of the elongation product obtained in b), wherein the product of step b) comprises a plurality of polynucleotides and each of said polynucleotides is separated from the others differing in length by a single nucleotide.

2. The method of claim 1 wherein after step a) an annealing reaction between said template and a primer able to hybridize to said template is carried out.

3. The method of claim 2, wherein the nucleic acid template comprises at least one standard W-C base A, C, G, T or U and at least one base capable of base pairing and different from the standard W-C bases.

4. A method for determining the nucleotide base sequence of a nucleic acid template comprising at least one base capable of base pairing and different from the standard Watson-Crick (W-C) bases comprising:
   a) providing a nucleic acid template comprising at least one base capable of base pairing and different from the standard W-C bases;
   b) elongating said template using a primer or a promoter or a promoter and an initiator in the presence of a nucleic acid synthesizing enzyme, nucleic acid synthesizing enzyme substrates and nucleic acid enzyme substrate derivatives;
   c) determining the base sequence of the template as the reverse complement of the sequence of the elongation product obtained in b),
   wherein after step a) an annealing reaction between said template and a primer able to hybridize to said template is carried out,
   wherein the nucleic acid template comprises at least one standard W-C base A, C, G, T or U and at least one base capable of base pairing and different from the standard W-C bases, and
   wherein the base triphosphates different from the standard W-C bases are present at a different concentration than the standard W-C base triphosphates are present at in the elongation step b).

5. The method of claim 1, wherein the base capable of base pairing and different from the standard W-C bases is selected from the group consisting of: iso-C; iso-G; 2,6-diaminopyrimidine; xanthine; 6-amino-5-substituted pyrazin-2(1H)-one;
   1-methyl-pyrazolo [4,3-d]pyrimidine-5,7(4H,6H)-dione; 5-aza-7-deazaguanine;
   6-amino-3-substituted pyrazin-2(1H)-one;
   3-amino-1-methylpurin-2-one;2,4-diamino-5,6-dihydropyrimidine;
   2-amino-6-(N,N-dimethylamino)purine; pyridin-2-one;
   3-methyl isocarbostyril; 5-methyl isocarbostyril; 7-propynyl isocarbostyril; m-xylene; 1,3,4-trimethylbenzene; 2-methylanaphthalene; 1,4-dimethylnaphthalene; 1-methylanaphthalene; naphthalene; 7-azaindole; isocarbostyril; 6-methyl-7-asaindole;
   3-propynyl-7-azaindole; imidazopyridine; pyrrolopyridine and a heterocyclic base having a structural formula of

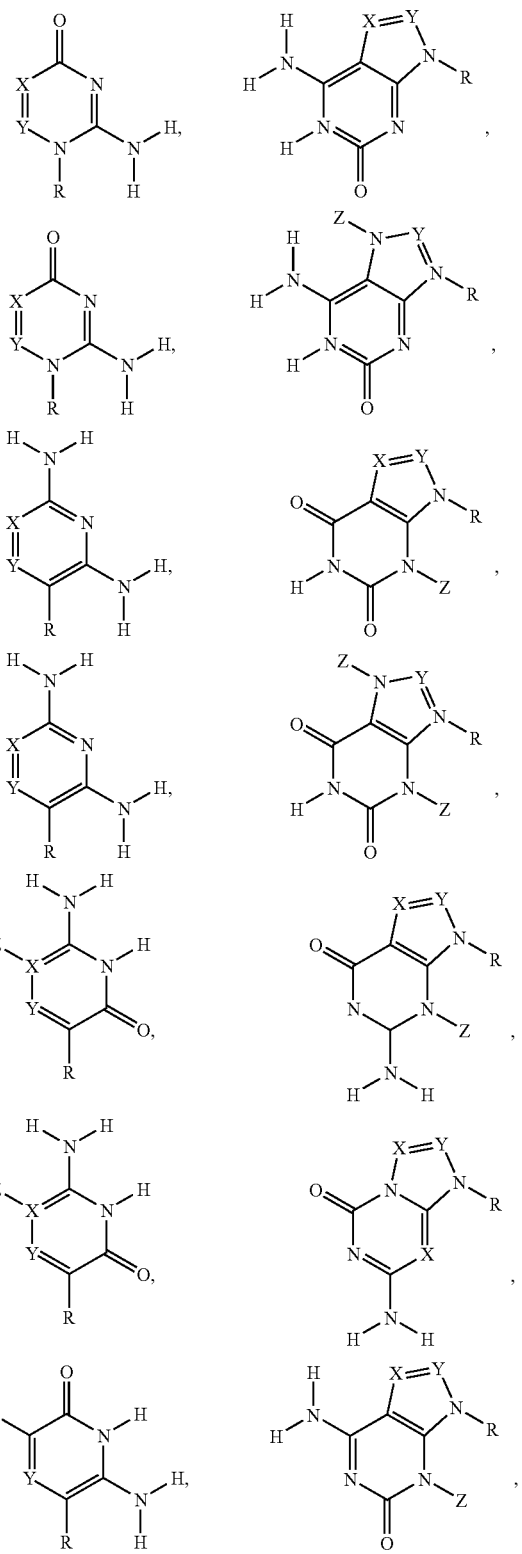

-continued

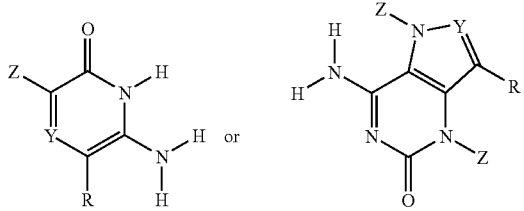

wherein R designates the point of attachment of the base to position 1 of a ribose or deoxyribose ring, X is either a nitrogen atom or a carbon atom bearing a substitutent Z. Z is either a hydrogen, an unfunctionalized lower alkyl chain, or a lower alkyl chain bearing an amino, carboxyl, hydroxyl, thiol, aryl, indole, or imidazolyl group, Y is either N or CH, and each ring contains no more than three nitrogens consecutively bonded.

6. The method of claim 1, wherein the base capable of base pairing and different from the standard W-C bases is isoC and/or isoG.

7. A method for determining the nucleotide base sequence of a nucleic acid template comprising at least one base capable of base pairing and different from the standard Watson-Crick (W-C) bases comprising:
  a) providing a nucleic acid template comprising at least one base capable of base pairing and different from the standard W-C bases;
  b) elongating said template using a primer or a promoter or a promoter and an initiator in the presence of a nucleic acid synthesizing enzyme, nucleic acid synthesizing enzyme substrates and nucleic acid enzyme substrate derivatives;
  c) determining the base sequence of the template as the reverse complement of the sequence of the elongation product obtained in b),
  wherein the base capable of base pairing and different from the standard W-C bases is isoC and/or isoG, and
  wherein the concentration of isoC and isoG triphosphate is lower than the concentration of the standard base triphosphates in the elongation step b).

8. The method of claim 1, wherein the template is DNA, the synthesizing enzyme is DNA-dependent DNA polymerase, the synthesizing enzyme substrate is a plurality of dNTPs and substrate derivatives comprise ddNTPs.

9. The method of claim 8, wherein a dNTP or a ddNTP is labeled.

10. The method of claim 9, wherein the primer or initiator is labeled.

11. The method of claim 9, wherein the label is an isotope, a chromophore or a fluorophore.

12. A method for determining the nucleotide base sequence of a nucleic acid template comprising at least one base capable of base pairing and different from the standard Watson-Crick (W-C) bases comprising:
  a) providing a nucleic acid template comprising at least one base capable of base pairing and different from the standard W-C bases;
  b) elongating said template using a primer or a promoter or a promoter and an initiator in the presence of a nucleic acid synthesizing enzyme, nucleic acid synthesizing enzyme substrates and nucleic acid enzyme substrate derivatives;
  c) determining the base sequence of the template as the reverse complement of the sequence of the elongation product obtained in b),
  wherein the template is DNA and the synthesizing enzyme is a DNA-dependent RNA polymerase, the synthesizing enzyme substrate is a plurality of NTPs and substrate derivatives comprise 3'-dNTPs derivatives.

13. The method of claim 12, wherein a NTP or a 3'-dNTP derivative is labeled.

14. The method of claim 12, wherein the primer or initiator is labeled.

15. The method of claim 13, wherein the label is an isotope, a chromophore or a fluorophore.

16. A method for determining the nucleotide base sequence of a nucleic acid template comprising at least one base capable of base pairing and different from the standard Watson-Crick (W-C) bases comprising:
  a) providing a nucleic acid template comprising at least one base capable of base pairing and different from the standard W-C bases;
  b) elongating said template using a primer or a promoter or a promoter and an initiator in the presence of a nucleic acid synthesizing enzyme, nucleic acid synthesizing enzyme substrates and nucleic acid enzyme substrate derivatives;
  c) determining the base sequence of the template as the reverse complement of the sequence of the elongation product obtained in b),
  wherein the template is RNA and the synthesizing enzyme is a RNA-dependent DNA polymerase, the synthesizing enzyme substrate is a plurality of dNTPs and the substrate derivatives comprise ddNTPs.

17. The method of claim 16, wherein a dNTP or a ddNTP is labeled.

18. The method of claim 17, wherein the primer or initiator is labeled.

19. The method of claim 17, wherein the label is an isotope, a chromophore or a fluorophore.

20. A method for determining the nucleotide base sequence of a nucleic acid template comprising at least one base capable of base pairing and different from the standard Watson-Crick (W-C) bases comprising:
  a) providing a nucleic acid template comprising at least one base capable of base pairing and different from the standard W-C bases;
  b) elongating said template using a primer or a promoter or a promoter and an initiator in the presence of a nucleic acid synthesizing enzyme, nucleic acid synthesizing enzyme substrates and nucleic acid enzyme substrate derivatives;
  c) determining the base sequence of the template as the reverse complement of the sequence of the elongation product obtained in b),
  wherein the template is RNA and the synthesizing enzyme is a RNA-dependent RNA polymerase, the synthesizing enzyme substrate is a plurality of NTPs and the substrate derivatives comprise 3'-dNTPs derivatives.

21. The method of claim 20, wherein a NTP or a 3'-dNTP derivative is labeled.

22. The method of claim 20, wherein the primer or initiator is labeled.

23. The method of claim 21, wherein the label is an isotope, a chromophore or a fluorophore.

24. A method for determining the nucleotide base sequence of a nucleic acid template comprising at least one base capable of base pairing and different from the standard Watson-Crick (W-C) bases comprising:
  a) providing a nucleic acid template comprising at least one base capable of base pairing and different from the standard W-C bases;
  b) labeling one end of said template;
  c) chemically degrading said labeled template;
  d) determining the length of the products obtained in c, obtaining the sequence of the template as the sequence of the incremental lengths of the products.

25. The method of claim 24, wherein the nucleic acid template comprises at least one standard W-C base and at least one base capable of base pairing and different from the standard W-C bases.

26. The method of claim 24, wherein the base capable of base pairing and different from the standard W-C bases is selected from the group consisting of: iso-C; iso-G; 2,6-diaminopyrimidine;
  xanthine; 6-amino-5-substituted pyrazin-2(1H)-one;
  1-methyl-pyrazolo[4,3-d]pyrimidine-5,7(4H,6H)-dione; 5-aza-7-deazaguanine;
  6-amino-3-substituted pyrazin-2(1H)-one;
  3-amino-1-methylpurin-2-one; 2,4-diamino-5,6-dihydropyrimidine;
  2-amino-6-(N,N-dimethylamino)purine; pyridin-2-one;
  3-methyl isocarbostyril; 5-methyl isocarbostyril; 7-propynyl isocarbostyril; m-xylene; 1,3,4-trimethylbenzene; 2-methylnaphthalene; 1,4-dimethylnaphthalene;
  1-methylnaphthalene; naphthalene; 7-azaindole; isocarbostyril; 6-methyl-7-asaindole;
  3-propynyl-7-azaindole; imidazopyridine; and pyrrolopyridine and having a hetrocyclic base having a structural formula of

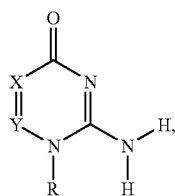
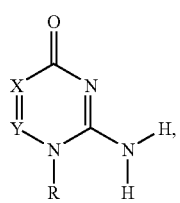
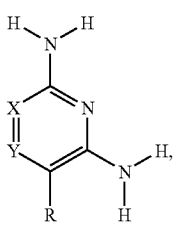
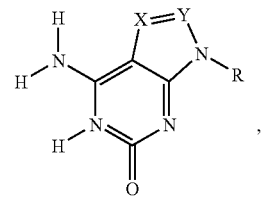
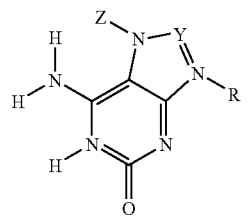
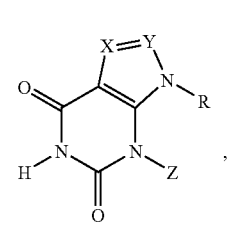
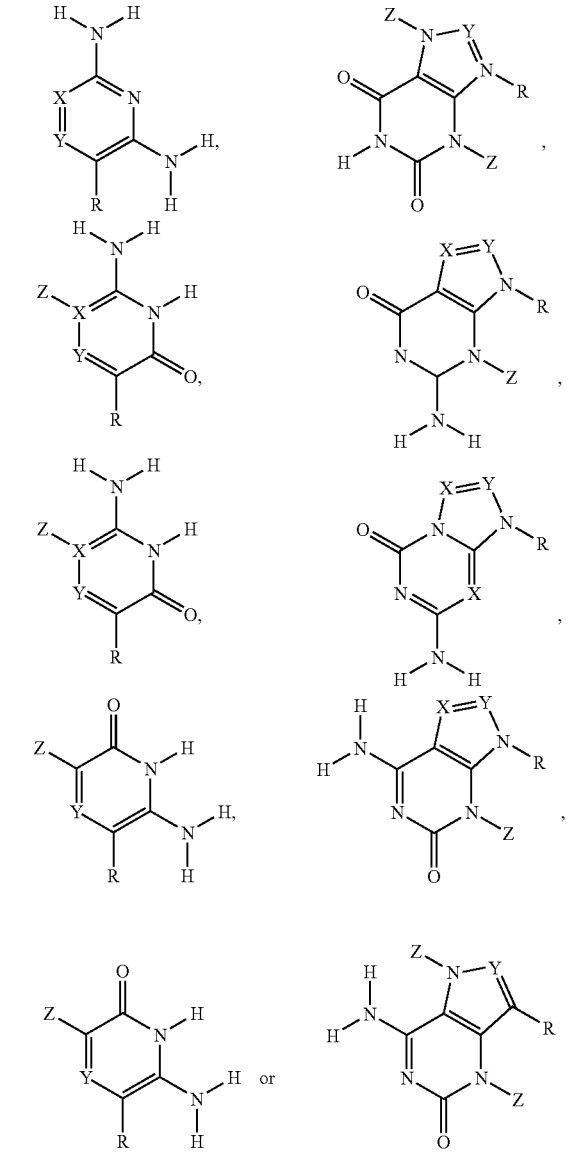

wherein R designates the point of attachment of the base to position 1 of a ribose or deoxyribose ring, X is either a nitrogen atom or a carbon atom bearing a substitutent Z. Z is either a hydrogen, an unfunctionalized lower alkyl chain, or a lower alkyl chain bearing an amino, carboxyl, hydroxyl, thiol, aryl, indole, or imidazolyl group, Y is either N or CH, and each ring contains no more than three nitrogens consecutively bonded.

27. The method of claim 24, wherein the base capable of base pairing and different from the standard W-C bases is isoC and/or isoG.

28. A method for the determination of the base sequence of a nucleic acid template comprising at least one base capable of base pairing and different from the standard Watson-Crick (W-C) bases, comprising:
  A) providing a nucleic acid template comprising at least one base capable of base pairing and different from the standard W-C bases;

B) elongating said template using a primer or a promoter or a promoter and an initiator in the presence of a nucleic acid synthesizing enzyme, nucleic acid synthesizing enzyme substrates and nucleic acid synthesizing enzyme substrate derivatives, to produce a plurality of polynucleotides;

C) separating polynucleolides differing in length by a single polynucleotide and determining the base sequence of the separated polynucleotides using MALDI-TOF-MS analysis.

29. A method for the determining the base sequence of a nucleic acid template comprising at least one base capable of base pairing and different from the standard Watson-Crick (W-C) bases,:

a) providing a nucleic acid template comprising at least one base capable of base pairing and different from the standard W-C standard bases;

b) carrying out elongation by using a primer, a promoter, or a promoter and initiator in the presence of nucleoside triphosphates whose base comprises at least one base capable of base pairing and different from the standard W-C bases by adding a first nucleoside triphosphate and detecting PPi release and degrading the first nucleoside triphosphate, then adding a second nucleoside triphosphate and detecting PPi and degrading the second nucleoside triphosphate, and repeating the procedure according to the kind of base of the nucleoside triphosphates provided;

c) repeating step b) above according to the template bases number desired to be sequenced;

d) determining the sequence of the template as the sequence of the nucleoside triphosphates added.

30. A method for determining the base sequence of a nucleic acid template comprising at least one base capable of base pairing and different from the standard Watson-Crick (W-C) bases,:

a) providing a plurality of oligonucleotides fixed on a chip, the oligonucleotides comprising at least one base capable of base pairing and different from the standard W-C bases and having overlapping frames displaced by one or two bases;

b) hybridizing the oligonucleotides with a labeled template according to the invention comprising at least one base capable of base pairing and different from the standard W-C bases;

c) detecting the signal of the label;

d) determining the sequence of the template as the set of overlapping oligonucleotides that are labeled.

* * * * *